US011103178B1

(12) United States Patent
Buckler et al.

(10) Patent No.: US 11,103,178 B1
(45) Date of Patent: Aug. 31, 2021

(54) METHOD AND APPARATUS FOR ANOSMIA PROGNOSTIC SCREENING

(71) Applicant: Avrio Genetics, Allentown, PA (US)

(72) Inventors: George Buckler, Phoenix, AZ (US); Jovan Hutton Pulitzer, Frisco, TX (US); James Strader, Austin, TX (US); Brandon Hensinger, Allentown, PA (US)

(73) Assignee: Avrio Genetics, Allentown, PA (US)

( * ) Notice: Subject to any disclaimer, the term of this patent is extended or adjusted under 35 U.S.C. 154(b) by 0 days.

(21) Appl. No.: 17/183,948

(22) Filed: Feb. 24, 2021

Related U.S. Application Data

(60) Provisional application No. 63/111,420, filed on Nov. 9, 2020.

(51) Int. Cl.
*G08B 21/00* (2006.01)
*A61B 5/00* (2006.01)
*G16H 20/13* (2018.01)
*A61B 5/117* (2016.01)
*G07C 9/20* (2020.01)
*G01N 33/00* (2006.01)

(52) U.S. Cl.
CPC ............ *A61B 5/4011* (2013.01); *A61B 5/117* (2013.01); *G01N 33/0001* (2013.01); *G07C 9/20* (2020.01); *G16H 20/13* (2018.01); *A61B 5/4005* (2013.01); *A61B 5/7495* (2013.01); *A61M 2205/588* (2013.01)

(58) Field of Classification Search
CPC ..... A61B 5/4011; A61B 5/117; A61B 5/7495; A61B 5/4005; G07C 9/20; G16H 20/13; A61M 2205/588

USPC ......................................................... 340/5.8
See application file for complete search history.

(56) References Cited

U.S. PATENT DOCUMENTS

| 6,325,475 | B1 * | 12/2001 | Hayes ..................... A61B 5/00 128/203.11 |
| 10,667,739 | B2 * | 6/2020 | Mochizuki ........... A61B 5/4011 |
| 2007/0077204 | A1 * | 4/2007 | Devanand .............. A61K 49/00 424/9.2 |
| 2013/0141211 | A1 * | 6/2013 | Troff .................... A47L 11/4008 340/5.21 |
| 2016/0220165 | A1 * | 8/2016 | Taherkhani .......... A61B 5/4011 |
| 2016/0287161 | A1 * | 10/2016 | Smith .................. A61B 5/4011 |
| 2017/0290541 | A1 * | 10/2017 | Albers ................. A61B 5/7475 |

* cited by examiner

*Primary Examiner* — Mark S Rushing

(57) ABSTRACT

An access system has a scanner that scans a unique identifier to access a location. A display receives an input. An automated dispenser dispenses at least one scent on each hand of an individual responsive to a control signal. A processor controls access to the location. A memory stores a set of instructions that configures the processor to receive the unique identifier from the scanner, actuate the automated dispenser to dispense the at least one scent responsive to receipt of the unique identifier, receive the response input based on the scents detected by the individual of the at least one scent, determine a passing result or a failing result responsive to the received response input and an expected response based on the dispensed at least one scent, enable access to the location responsive to a passing result and deny access to the controlled access location responsive to a failing result.

20 Claims, 23 Drawing Sheets

| ID | Control | Scent | Result | Date | Time |
|---|---|---|---|---|---|
| ABC | X | Coconut | X | XX/XX/XX | 10:00 |
| EFG | X | Coffee | O | XX/XX/XX | 10:00 |
| KLM | X | Orange | X | XX/XX/XX | 10:00 |
| RST | X | Coffee | X | XX/XX/XX | 10:00 |
|  | X | ROSE | X | XX/XX/XX | 10:00 |

METHOD AND APPARATUS FOR ANOSMIA PROGNOSTIC SCREENING

CROSS-REFERENCE TO RELATED APPLICATIONS

This application claims benefit of U.S. Provisional Application No. 63/111,420, filed Nov. 9, 2020, entitled METHOD AND APPARATUS FOR ANOSMIA PROGNOSTIC SCREENING, the specifications of which are incorporated by reference herein in their entirety.

TECHNICAL FIELD

This invention is related in general to utilizing the olfactory senses to detect health conditions and, more practically, utilizing the smell function (Anosmia) to detect indications of the presence of a virus.

BACKGROUND

Loss of smell function, referred to as "Anosmia," also known as smell blindness, involves the loss of the ability to detect one or more smells. This condition may be temporary or permanent and it differs from hyposmia, which is a decreased sensitivity to some or all smells. Anosmia can be due to a number of factors, including an inflammation of the nasal mucosa, blockage of nasal passages or a destruction of one temporal lobe. Inflammation is due to chronic mucosa changes in the lining of the paranasal sinus and in the middle and superior turbinates. Anosmia is reported to be associated with the novel coronavirus disease 2019 (COVID-19) infection.

In previously conducted smell research for COVID-19, a group of five odorants with maximum familiarity among 100 participants were selected for testing purposes. These five odorants were, coconut oil (O1), cardamom (O2), fennel (O3), peppermint (O4) and garlic (O5). These odorants were disposed in a crushed form (cardamom and fennel) or directly oil/chemical form (oil the case of coconut oil, menthol for peppermint and Di-allyl sulfide for garlic). The participants in the test were provided a bag containing the odorants along with a response sheet carrying a questionnaire about whether an individual can smell the odorants followed by identification of the smell if answered yes. The participants were chosen from a combination of asymptomatic (no comorbidities) COVID-19 positive individuals and control individuals. In certain circumstances, the tubes also included a blank (water) smell. It has been recognized that the presence of the COVID-19 virus results in an altered sense of smell or taste (anosmia/dysgeusia) for patients testing positive for the virus as compared to patients testing negative for the virus. In research, it has been reported that it is better to utilize direct measures of smell loss as opposed to self-reporting of smell loss. These direct measures involve having patients smell and report on actual odorants, whereas self-reporting methods include obtaining data through patient questionnaires, interviews, or electronic health records. Direct measures are considered objective, whereas self-reporting measures are subjective measures of a person's experience.

One of the basic Smell Identification Tests is that referred to as the "University of Pennsylvania Smell Identification Test (UPSIT). This is a simple and commercially available test which is considered to be reliable and practical. This has been administered internationally to more than 500,000 individuals. Recently, this test has been used in patients with COVID-19. This is a well-validated 40-odorant test. In applying this test to patients with COVID-19, it was demonstrated that decreased smell function, but not always anosmia, was a major marker for SARs-CoV-2 (COVID-19) infection and that smell testing may help, in some cases, to identify COVID-19 patients in need of early treatment or quarantine. When this test is combined with a fever check, routine screenings are improved. In general, it is considered that temperature checks alone are not a guarantee that individuals who do not have elevated temperatures also do not have COVID-19. It may be that the first indicator is loss of sense of smell. The reverse is also true: Feverish individuals might not have COVID-19.

These smell test can be as simple as scratch-and-sniff cards with a defined readily known odorant associated therewith. For example, the scent of a rose is very well known and can be utilized. And, again, it is recognized that just asking a patient if they have lost their sense of smell is less reliable than incorporating objective measurements of smell. The reason for this is that anosmia is quite specific to COVID-19 and provides a strong indication that an individual is infected with such.

SUMMARY

The present invention, as disclosed and described herein, in one aspect thereof, comprises a system for controlling access to a controlled access location includes a scanner that scans a unique identifier for access to the controlled access location. An input display receives a response input from an individual based upon the scents detected by the individual. An automated testing dispenser dispenses at least one testing scent on each hand of the individual desiring access to the controlled access location responsive to a dispensing control signal. A processor coupled to the automated testing dispenser, the scanner and the input display controls access to the controlled access location responsive to a stored set of instructions. A memory stores the set of instructions that configures the processor to receive the unique identifier from the scanner, generate the dispensing control signal to actuate the automated testing dispenser to dispense the at least one testing scent responsive to receipt of the unique identifier, receive the response input from the individual based on the scents detected by the individual of the at least one testing scent dispensed on their hands, determine a passing test result or a failing test result responsive to the received response input and an expected response based on the dispensed at least one scent, enable access to the controlled access location responsive to a determined passing test result and deny access to the controlled access location responsive to a determined failing test result.

BRIEF DESCRIPTION OF THE DRAWINGS

For a more complete understanding, reference is now made to the following description taken in conjunction with the accompanying Drawings in which.

DETAILED DESCRIPTION

Figure 1:
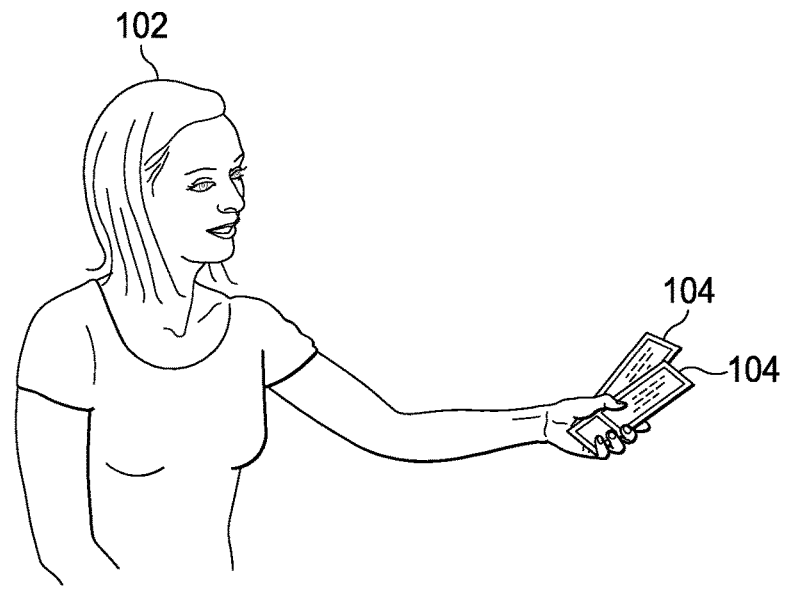
FIG. 1 illustrates a diagrammatic view of a user attempting to gain access to a venue and possessing tickets.

Referring now to the drawings, wherein like reference numbers are used herein to designate like elements throughout, the various views and embodiments of Method and Apparatus for Anosmia Prognostic Screening are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

In the various disclosed embodiments, an individual desiring to gain access to any given venue or location is required to pass through some type of screening point with one or more tickets, each having a unique and discrete ticket number or some type of code that uniquely identifies the individual possessing a ticket as having purchased the ability to gain access. However, for health concerns, certain health screening may be required in order to allow an individual to gain access to any venue wherein a large number of people may be gathered. It may be that this access is for any other reason also. This health screening can be performed at any level by person or a machine that can collect some type of biometric data from the individual or a predetermined analytic purpose, such as that associated with determining if an individual has some type of virus. The biometric data that may be collected can be in any form, depending upon what biometric data provides the desired information required by the analytic algorithm utilized by the operator or machine.

Referring now to FIG. 1, there is illustrated a user 102 having two tickets 104 contained on their person, these tickets 104 having indicia disposal surface thereof indicating some unique code that allows the user 102 access to a particular venue or location. These tickets 104 are unique and, as such, uniquely identify the user. These tickets typically contain some type of barcode that, when scanned into a system, identifies these tickets as valid tickets to the venue and will typically indicate a seat and row in the venue. There is a database at some remote location (or at a local location) that contains information identifying the individual that purchased or obtained this particular ticket, such that cross reference can be made if required. If necessary, this information can actually assist in locating this particular individual within a large venue via the location information associated with that particular ticket.

Figure 2:
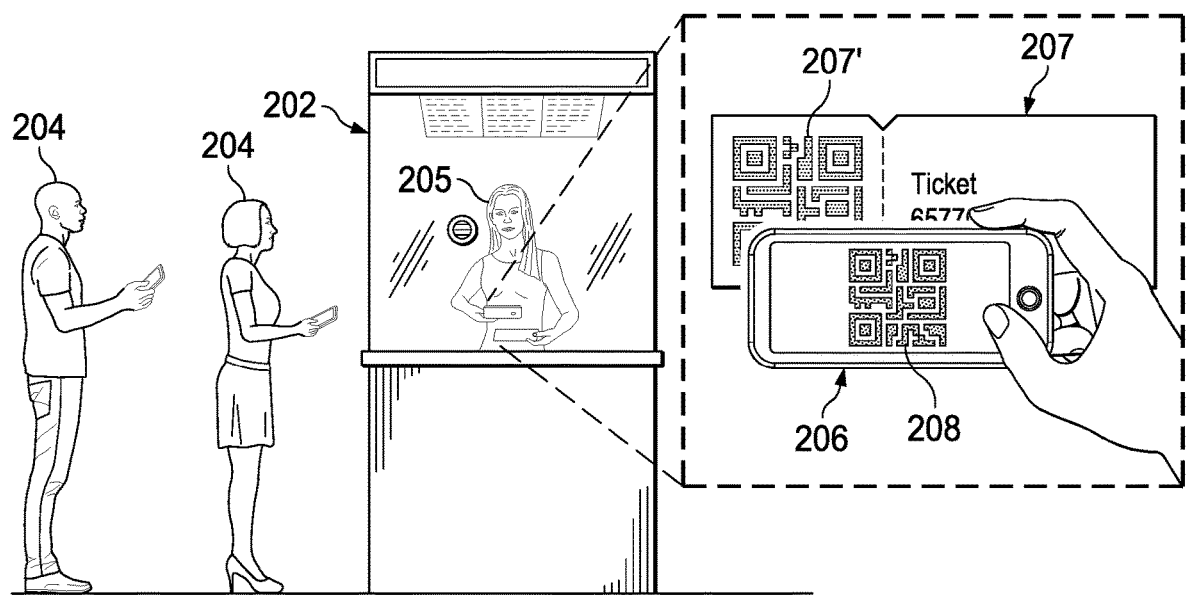
FIG. 2 illustrates a diagrammatic view of an access gate at which a ticket containing a barcode is presented to an attendant.

Referring to FIG. 2, there is illustrated a diagrammatic view of the ticket booth 202 through which individuals 204 must pass in order to gain access. Each of the individuals 204 possesses a ticket 207 having disposed thereon a unique barcode 207'. An attendant 205 at the ticket booth 202 has a scanning device 206 which, in this disclosed embodiment is a mobile phone with the display, that is operable to scan the ticket 207, and the barcode 207' in order to obtain an image 208 on the display of the gain device 206. This is then transmitted to a central location for confirmation. This is the confirmation process that will be disclosed hereinbelow. Once confirm, the individuals 204 are allowed to gain access through an entry gate and complete the check-in process.

Figure 3:
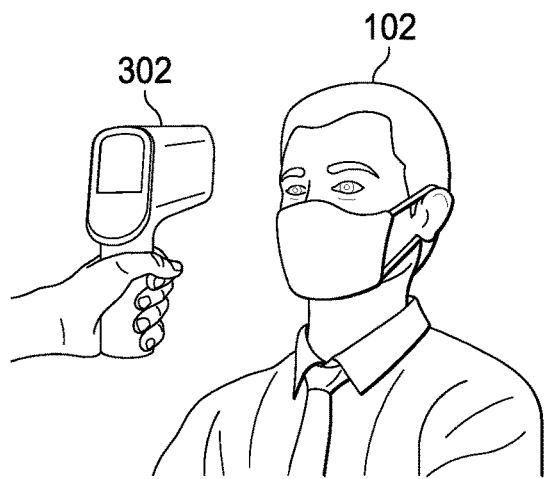
FIG. 3 illustrates a diagrammatic view of a temperature scan of the user.

Referring now to FIG. 3, at this location or event, various screening techniques for viruses such as COVID-19 may be deployed. One such is depicted as a temperature scanner 302 for scanning the forehead of the individual 102. This is one biometric indicator of the presence of some possible infection. This infection could, of course, result from a person being positive for COVID 19 or any other infection, such as the common cold. However, this is merely a test that triggers other tests and is not necessarily indicative of an individual being positive for COVID 19. Additional screening tests may be required and, as we disclosed hereinbelow, these additional tests are tests that are very specific for COVID 19.

Figure 4:
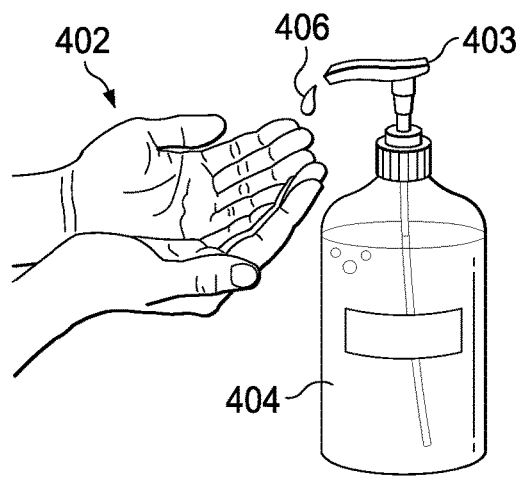
FIG. 4 illustrates a diagrammatic view of the user sanitizing their hands.
Figure 5:
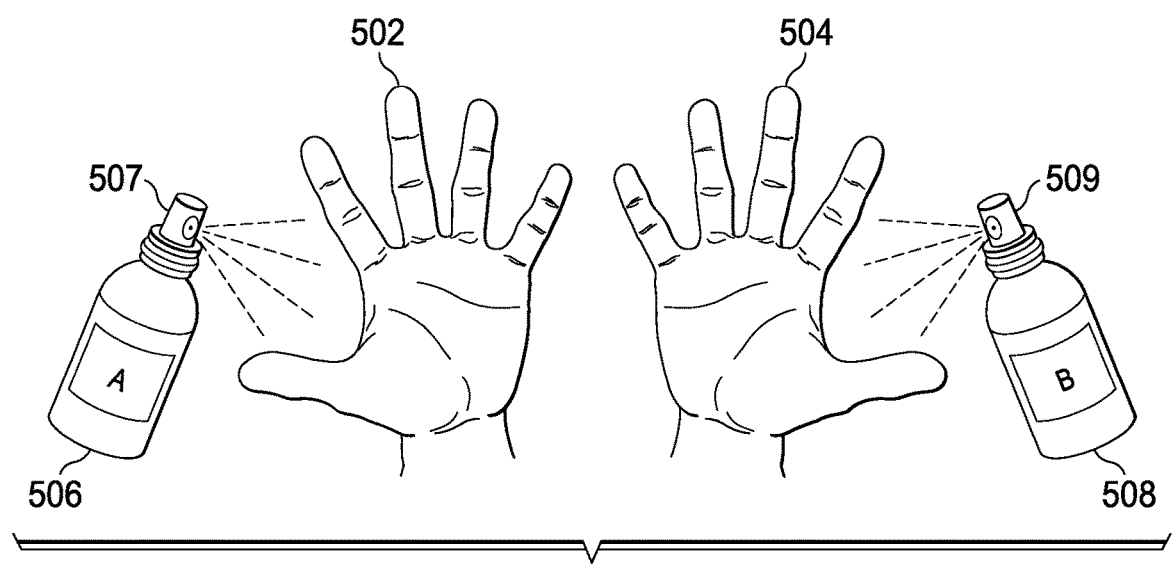
FIG. 5 illustrates a diagrammatic view of one embodiment wherein two different anti-septic sprays are utilized, one for each hand.

Referring to FIG. 4, there is illustrated diagrammatic view of a health screening program associated with a smell test for the detection of an individual having anozmia as will be described in more detail hereinbelow. In this reading, one goal is to achieve a rapid anozmia screen that can be deployed as part of a non-invasive screening measure. In this depicted embodiment, the individual's hands 402 are disposed under a dispenser 403 of a reservoir 404 containing some type of antiseptic compound. This can be a touchless system wherein a specified amount 406 of the compound stored in the reservoir 404 is dispensed onto the hand or hands 402 of the individual. This specified amount 406 of the compound can be either an antiseptic spray or even a gel. The dispenser can be a touchless dispenser is activated by the individual or an operator can be associated with the overall process and manually activate the dispenser 403 to dispense the specified amount 406 of the compound stored in the reservoir 404. An "odorant" is combined with the antiseptic spray within the reservoir 404.

Figure 6A:
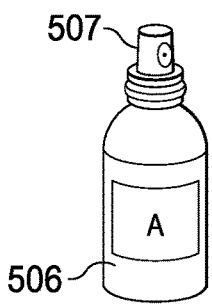
FIGS. 6A and 6B illustrate the two different antiseptic sprays in diagrammatic views.
Figure 6B:
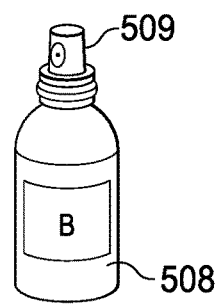

Referring to FIGS. 6A and 6B, there illustrated details of the two reservoirs 506 and 508. In one disclosed embodiment, it may be that the reservoir 506 contains no odorant and the other reservoir 508 contains a specific odorant additive formulation. This odorant is used to exploit hyposmia and anozmia in asymptomatic COVID 19 patients by using these added odorants. The basic compound can, and one environment, the ethanol (ethyl alcohol) or isopropyl alcohol (isopropanol or 2-propanol). Reservoir 506 will contain only this basic compound. Reservoir 508, on the other hand, has added thereto any of the multiple University of Pennsylvania Smell Identification Test (UPSIT) stimuli for smell (of which there are approximately 40) or any relative combinations thereof. This UPSIT test is a test that is commercially available for smell identification to test the function of an individual's olfactory system. The test is usually administered in a waiting room and takes only a few minutes. The test consists of 4 different 10 page booklets, with a total of 40 questions. On each page, there is a different "scratch and sniff" strip which are embedded with a micro encapsulated odorant. There is also a 4 choice multiple-choice question on each page. The scents are released using a pencil. After each scent is released, the patient smells a level and detects the odor from the four choices. There is an answer column on the back of the test booklet, and the test is scored out of 40 items. The score is compared to scores in a normative database from 4000 normal individuals, which tells the level of absolute smell function. The score also indicates how the patient does in accordance to their age group and gender.

As part of a non-invasive health screening process, and individual seeking entry has a hand-sanitizer sprayed on each of a left-hand 502 and a right-hand 504 from separate reservoirs 506 and 508. The reservoir 506 has a dispenser 507 that is independently activated to provide a spray to the left-hand 502. Similarly, the reservoir 508 has a dispenser 509 that is independently activated to provide a spray to the right hand 504. Again, as described hereinabove, this can be done via a touchless automated system or by third party entry confirmation individual. The samples are labeled A for reservoir 506 and B for reservoir 508.

Figure 7:
FIG. 7 illustrates a diagrammatic view of the smell test.

Once the entrants hands are sprayed, they will be asked to smell both hands individually and to let the person administering the test then inquire "what do you smell?" or "what scent can you smell on your hands?" It is important that the individual not rub their hands together or mix the two administered sprays. Thus, in one embodiment, the compound is administered as a spray and, another embodiment, it could be a gel. In the case of the gel, it is important that the individual does not rub their hands together. They merely smell the gel before it is rubbed in. This is illustrated in FIG. 7. The individual, under normal health conditions, should be able to discern between the smells of the right and left hands and ideally pick up at least one unique smell (added odorant) on the opposite hand. If the individual can correctly identify by smell the added odorant, then the screening operation is to be considered valid and verified and the person is allowed to enter the venue or facility. If, however, the individual cannot correctly identify by smell the added odorant, then the screening test is to be considered to have identified through olfactory screening an individual which "may" have a specific "disease or infection state" and will need to repeat the screening test.

Figure 8:
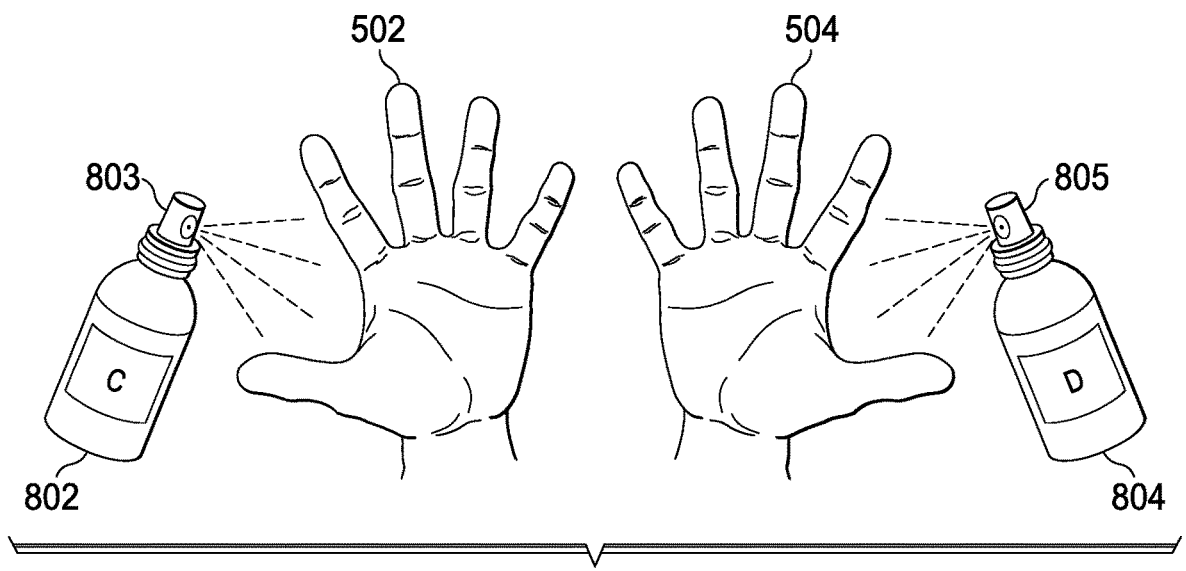
FIG. 8 illustrates a diagrammatic view of a following test.

Once the individual has failed initial screening test, he or she is subjected to an additional screening test utilizing one or more newly added odorant-modified hand sanitizers. This odor test enables monitored self-reporting, used as early identification and isolation of asymptomatic/pre-symptomatic cases are patients with mild symptoms (who may not have a fever). In this additional test, the entrants have their hands again sprayed with two new odorant-modified hand sanitizers and asked to discern between the smells of the two hands and ideally pick up two unique smells, but at least one unique smell. This process is illustrated in FIG. 8, wherein two additional reservoirs 802 and 804 are provided with dispensers 803 and 805, respectively, for spraying on the respective left and right hands 502 and 504. Again, these dispensers 803 and 805 can be touchless sprays or third-party activated. It is undesirable for the user to actually touch these dispensers 803 or 805.

Figure 9:
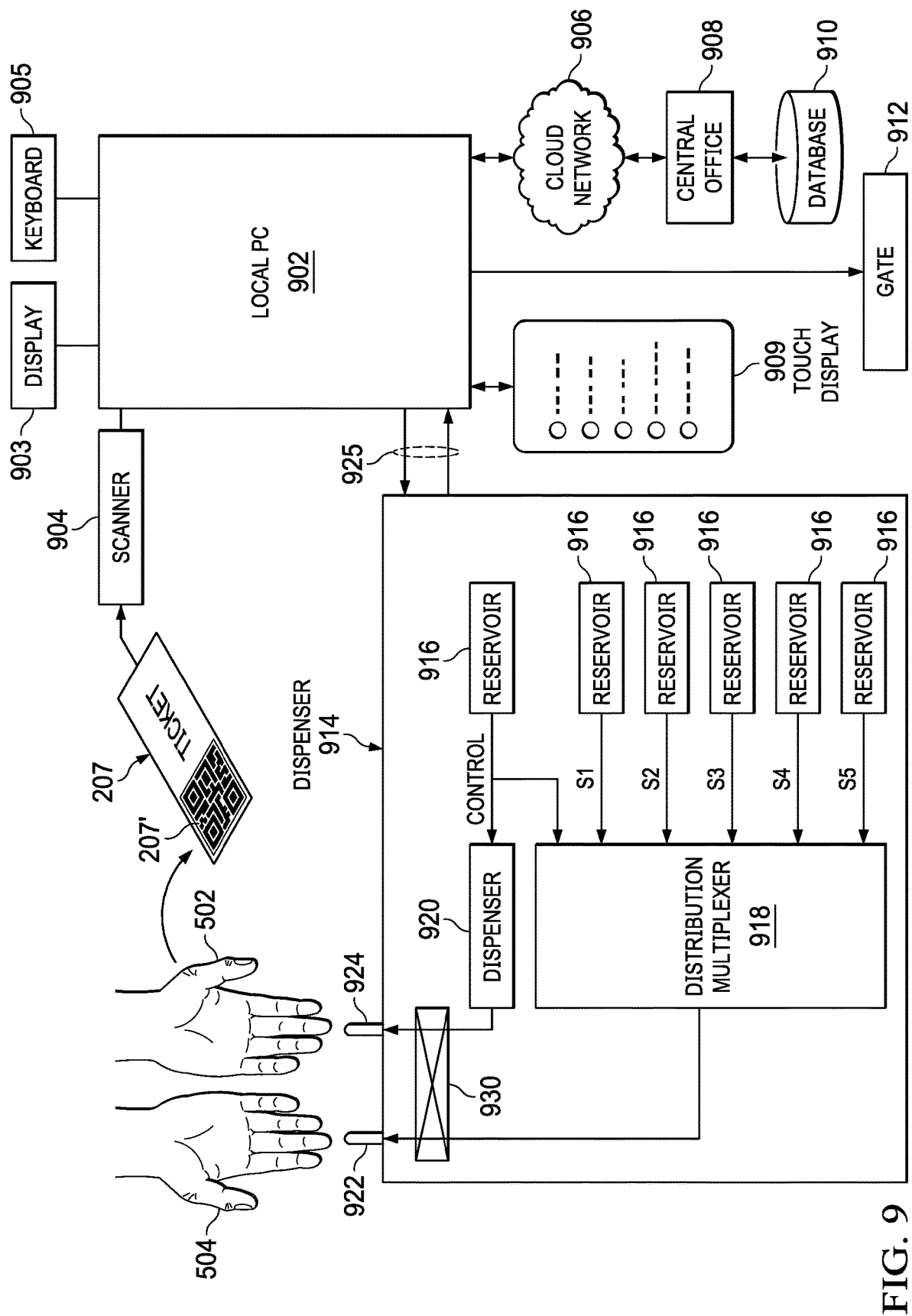
FIG. 9 illustrates a diagrammatic of an overall system in one disclosed embodiment.

Referring now to FIG. 9, there is illustrated a diagrammatic view of an overall system in one disclosed embodiment. The ticket 207 is utilized by the individual with that the unique barcode or ID 207' to gain access at an entry gate. The ticket 207 and the barcode 207' are input to a scanner 904 to scan the information there from. The scanner 904 is interface with a local processor or PC 902, which is operable to interface with an operator the a display 903 and a keyboard or other input device 905. The local PC 903 also interfaces to a central office 908 through a cloud network 906 such as the Internet. The central office 908 has a database 910 associated there with for storing information regarding the ticket 207 in association with such things as the venue or event location, the seat and row location in the venue, the user, the time and date of purchase, the time and date of actual access grant, etc. This is stored in a relational database. In addition, there is stored in association there with information regarding the particular screening process which, in this particular disclosed embodiment, is a COVID 19 screening process. The local PC 902 is operable interface with a gate 912, in some situations, wherein the gate 912 is all likely control to grant or deny access. A touch display 909 is also controlled by the local PC 902 enrolled order to allow interface with the individual that is desirous of gaining access to the venue or event.

A dispenser 914 is provided which has contained therein a plurality of reservoirs 916. These are reservoirs 916 contain antiseptic spray or gel and an odorant or, in the case of a control, a lack of an odorant. For example, five of the reservoirs 916 have odorants associated there with, the outputs labeled S1, S2, S3, S4 and S5, and one of the reservoirs 916 labeled Control. The five reservoirs 916 containing odorants are input to a distribution multiplexer 918 for selective dispensing. The dispensing multiplexer is operable to select one of the outputs of the 5 odorant containing reservoirs 916 for interface with an internal pump or activation mechanism to allow the selected odorant containing antiseptic to be dispensed via an orifice 922. Similarly, the reservoir 916 containing the Control is input to a dispenser 920 which can be selectively activated to dispense the contents of the reservoir 916 containing no odorant, i.e., the control reservoir, out of an orifice 924. Again, as described above, this could be a spray of an alcohol-based antiseptic or a gel-based antiseptic which has as a base a glycerin compound. Typically, the antiseptic will be approximately 70% or greater in alcohol content.

It should be understood that the odorant can be contained in a reservoir with antiseptic as a standalone compound or, alternatively, it could be that the reservoir contains nearly the odorant and is next with a control.

In operation, the individual is instructed to dispose your hands under the orifices 922 and 924 and, in one embodiment utilizing touchless distribution, and can be sensed by a sensor (not shown) and the appropriate pumps activated by the local PC 902. The local PC 902 has control/sense lines 925 associated there with to send control signals to the dispenser 914 and receives signals from the dispenser 914. When the user places their hands under the dispenser 914 for touchless or third-party operator control, the local PC 902 determines which of the odorants are distributed. One aspect of the overall system is that it is important that the individual not have a predetermined knowledge of the odorant utilize. For example, they may hear the person in front of them exclaim "that smells like coconut." Thus, it is important that the same odorant not be utilized for sequential people.

After the individual has been instructed to smell each hand before rubbing their hands together, the individual is presented with choices on the touch display 909. For this operation, and this particular disclosed display, only a single set of choices is displayed. Thus, all that is being inquired about is whether they can discern (smell) any odorant. They will be provided with, for example, 5 selections from which they are to choose. Since the local PC 902 has determine which odorant is dispensed, it is possible to present the correct choice among others. The 5 choices do not necessarily have to represent the 5 odorants are available, as it is only necessary that the dispensed odorant is on the set of choices. If an odorant is dispensed to both hands, to sequential displays of 5 choices can be provided or choices for the left-hand and right-hand can be provided.

Additionally, there is provided a multiplexer 930 that will allow the distribution multiplexer 918 to output odorant-enhanced antiseptic spray on either the orifice 922 or the orifice 924. Thus, it is possible to dispense two odorants in sequence. Additionally, the control can be interfaced with the distribution multiplexer 918 on the input thereof, such that the the control can be dispensed via the distribution multiplexer 918. In one operation, before any distribution, both the distribution multiplexer 918 and the orifice 922 are flushed with the control antiseptic that has no odorant in there. The reason for this is that it is desirable that what is dispensed does not have odorant from a previous dispensing operation. Thus, after each operation of the distribution multiplexer 918, and after the user has removed their hands, a small amount of control is routed to the input of the distribution multiplexer 918 for distribution from the orifice 922. This will ensure that the output of the distribution multiplexer 918 and the orifice 922 are devoid of any odorant-enhanced antiseptic compound from a previous distribution or dispensing operation. All of these operations are controlled and recorded by the local PC 902. They are all linked in the relational database with the unique ID of the ticket number. Thus, they are effectively link to the actual individual.

In the event that additional test is required wherein two odorant-enhanced antiseptic compounds are required to be dispensed, one to each hand, the multiplexer 930 can be operated to distribute one odorant-enhanced spray to one hand, flush the orifice 922 with control and then distribute a second odorant-enhanced rate to the other hand. Instructions will have to be dispensed to the individual. The orifices 922 and 924 can be separated so that both hands can be disposed under the apparatus or they can be disposed in close association therewith, such that two operations will be required.

Figure 10:
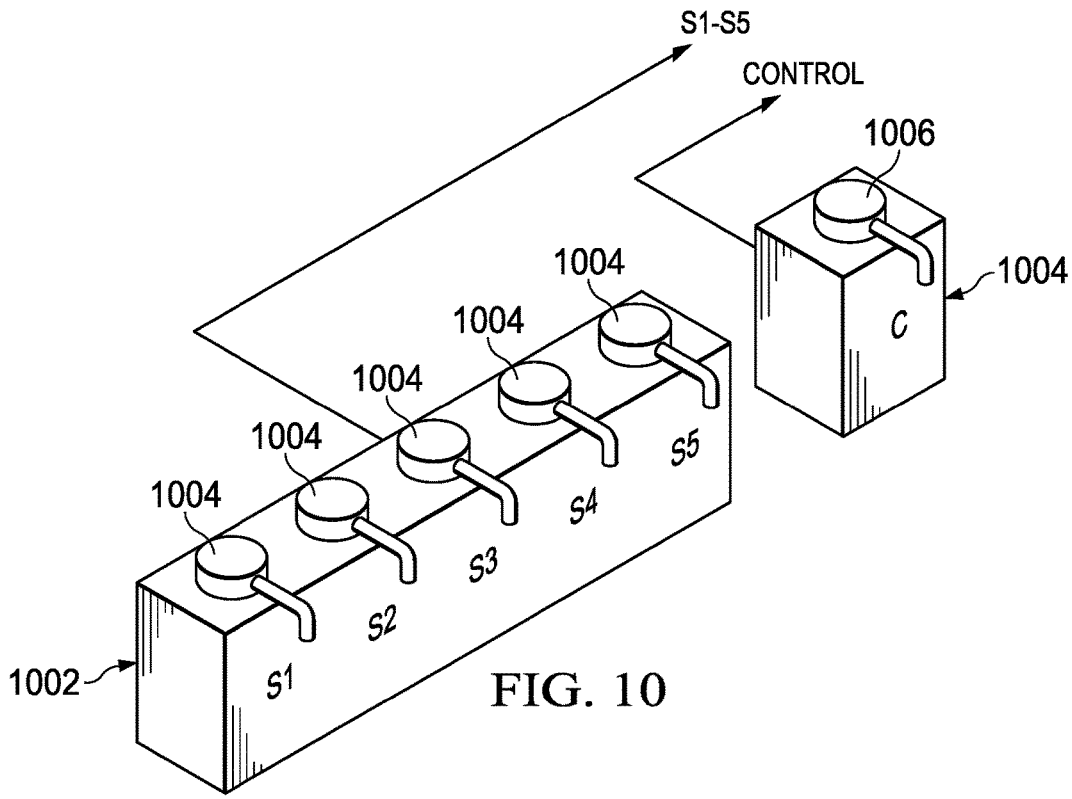
FIG. 10 illustrates a perspective view of an example of a dispenser of FIG. 9.

Referring now to FIG. 10, there is illustrated a perspective view of an example of a dispenser 914, which is comprised of a first dispenser 1002 and a second dispenser 1004. The first dispenser 1002 is operable to dispense the 5 odorant-enhanced antiseptic compounds in the second dispenser 1004 is operable to dispense the control antiseptic compound. Each of the 5 internal reservoirs (not shown) is associated with a dispensing nozzle 1004. The second dispenser 1004 has a single dispensing nozzle 1006 associated there with. These nozzles can be, as described hereinabove, associated with a touchless system or operator controlled by a third-party operator. It could be that the local PC 902 actually controls them or that it indicates to the operator which ones to push or that it senses which one the operator actually pushes, such that the operator can randomize the selection. However, this system allows an individual to see which one is being pushed and there is a possibility that someone in the back of line can see which one is pushed and somehow discern what odorant is associated therewith. It is possible that there may be a cover over the nozzles 1004 and 1006 such that it is impossible for a casual observer to determine which one has been pushed or selected. The local PC 902 can make the randomized selection completely unseen by any individual passing through the entry line. The local PC 902 removes any bias that could be injected by a third-party operator. For example, the third-party operator could be by the lackadaisical and merely push the same nozzle each time for dispensing of the same odorant-enhanced antiseptic compound each time. Additionally, it is possible that the third-party operator, having some idea as to what odorant is associated with any particular reservoir, could allow friends to pass through, i.e., allow them to pass the test and gain access regardless of their health condition. It may be that any regulating body would require removal of individual bias with an independent processor-based system.

Figure 11:
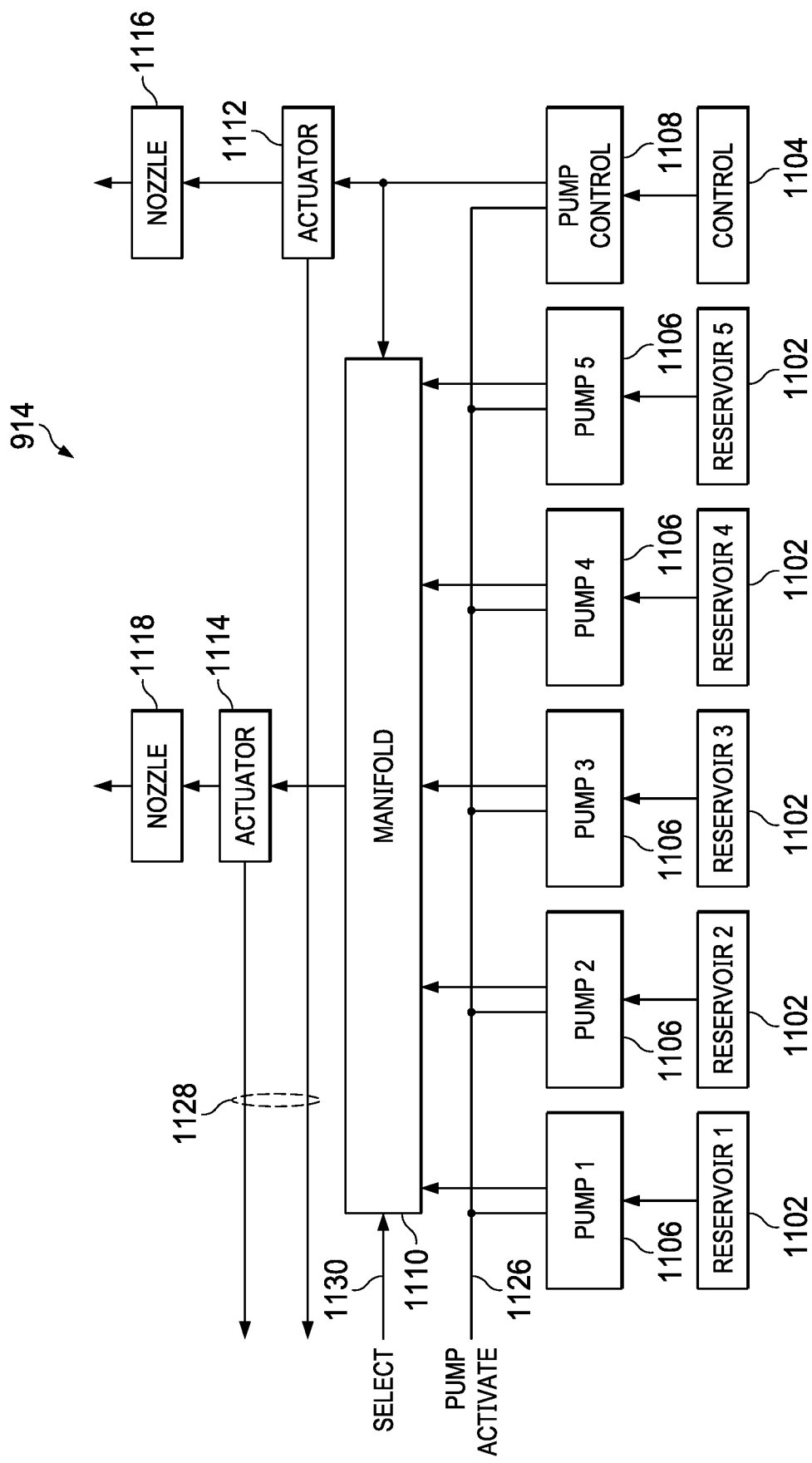
FIG. 11 illustrates one example of the detail of the dispenser of FIG. 9.

Referring to FIG. 11, there is illustrated one example of the detail of the dispenser 914. As noted above, there are illustrated five odorant-enhanced antiseptic compound reservoirs 1102 in a single control antiseptic compound reservoir 1104. Each of the owner-enhanced antiseptic compound reservoirs 1102 by interface with a separate and associated pump 1106 and the control antiseptic compound reservoir 1106 is interface with a pump 1108. The reservoirs 1102 and 1104 can be pressurized reservoirs wherein the pumps merely require the depression of a nozzle to release the pressurized contents or they can be a mechanical spray or dispenser mechanism that requires a reciprocating pump action. These are well-known type of pumping mechanisms however, each of the pumps is activated by the local PC 902 via a control line 1126, each controlled independently. Each of the pumps 1106 and 1108 has the output thereof interfaced with a manifold 1110, which is equivalent to the distribution multiplexer 918 of FIG. 9. This is operable to select the output of any one of the pumps 1106-1108 for output thereof to an actuator sense block 1112. The actuator sense block 1112 is associated only with the output of the pump 1108, whereas the actuator sense block 1114 is interface with the output of the manifold 1110. The actuator sense blocks 1112 and 1114 provide feedback via sense lines 1128 to the local PC 902 to indicate actuation thereof. The output of the actuator sense block 1112 is output to a nozzle 1116, this being the control nozzle and the output of the actuator sense block 1114 is output to a nozzle 1118, this being usually associated with the odorant-enhanced antiseptic compounds. As described hereinabove, the overall operation can allow for any one of the odorant-enhanced antiseptic compounds to be output from the nozzle 1118 in addition to the contents of the control reservoir 1104. This inclusion of the control antiseptic compound thus allows the manifold 1110 and the nozzle 1118 to be flushed out with the control antiseptic compound prior to dispensing of any odorant-enhanced antiseptic compound. Although not illustrated, it is possible that the output of the manifold 1110 could be Interface with the actuator 1112, if it were desirable to have the odorant-enhanced antiseptic compound dispensed from the nozzle 1116.

Figure 12:
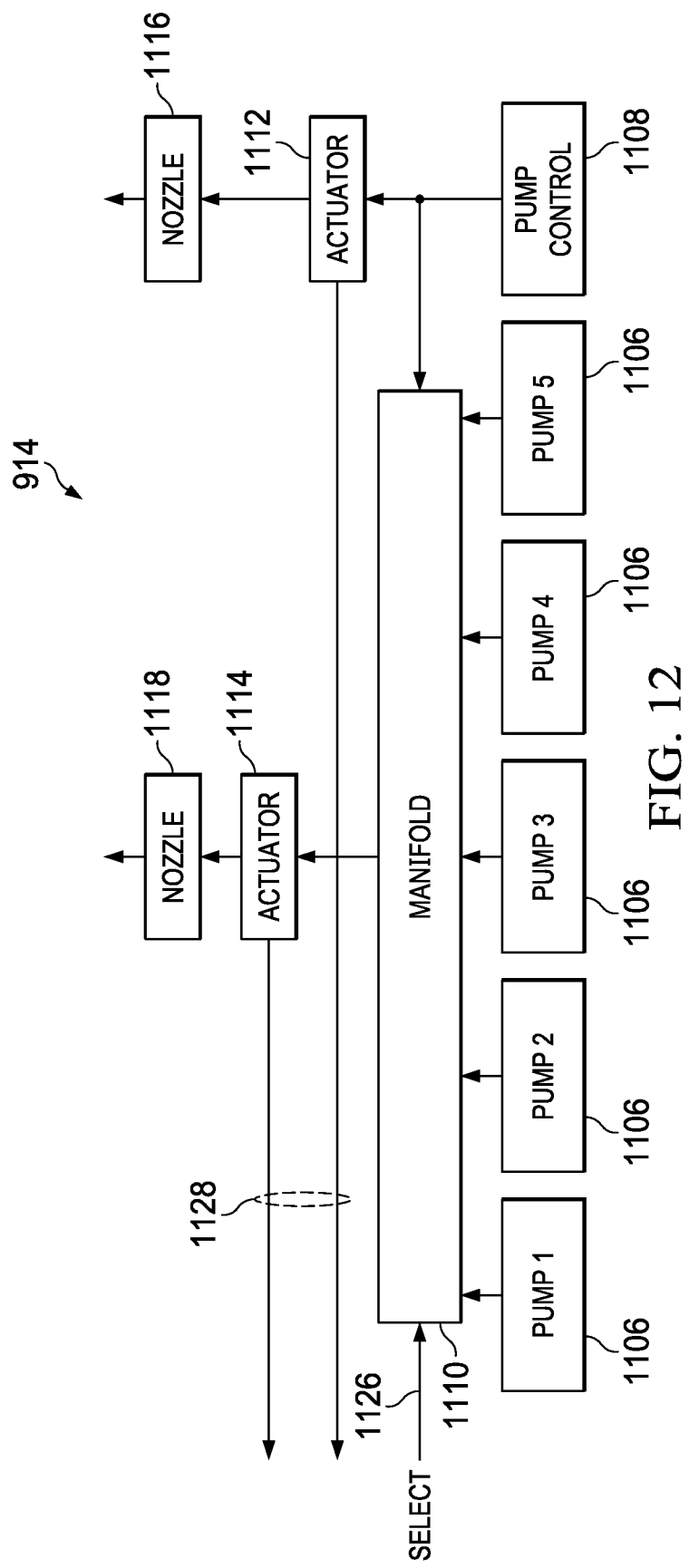
FIG. 12 illustrates an alternate embodiment wherein the manifold of FIG. 11 has two outputs.

Referring now to FIG. 12, there is illustrated an alternate embodiment wherein the manifold 1110 has two outputs, one output input to the actuator sense block 1114 and the other output input to the actuator sense block 1112. All 6 pump outputs from pumps 1106 and 1108 are input to the manifold 1110, such that manifold 1110 controls distribution to the respective nozzles 1118 and 1116.

Figure 13:
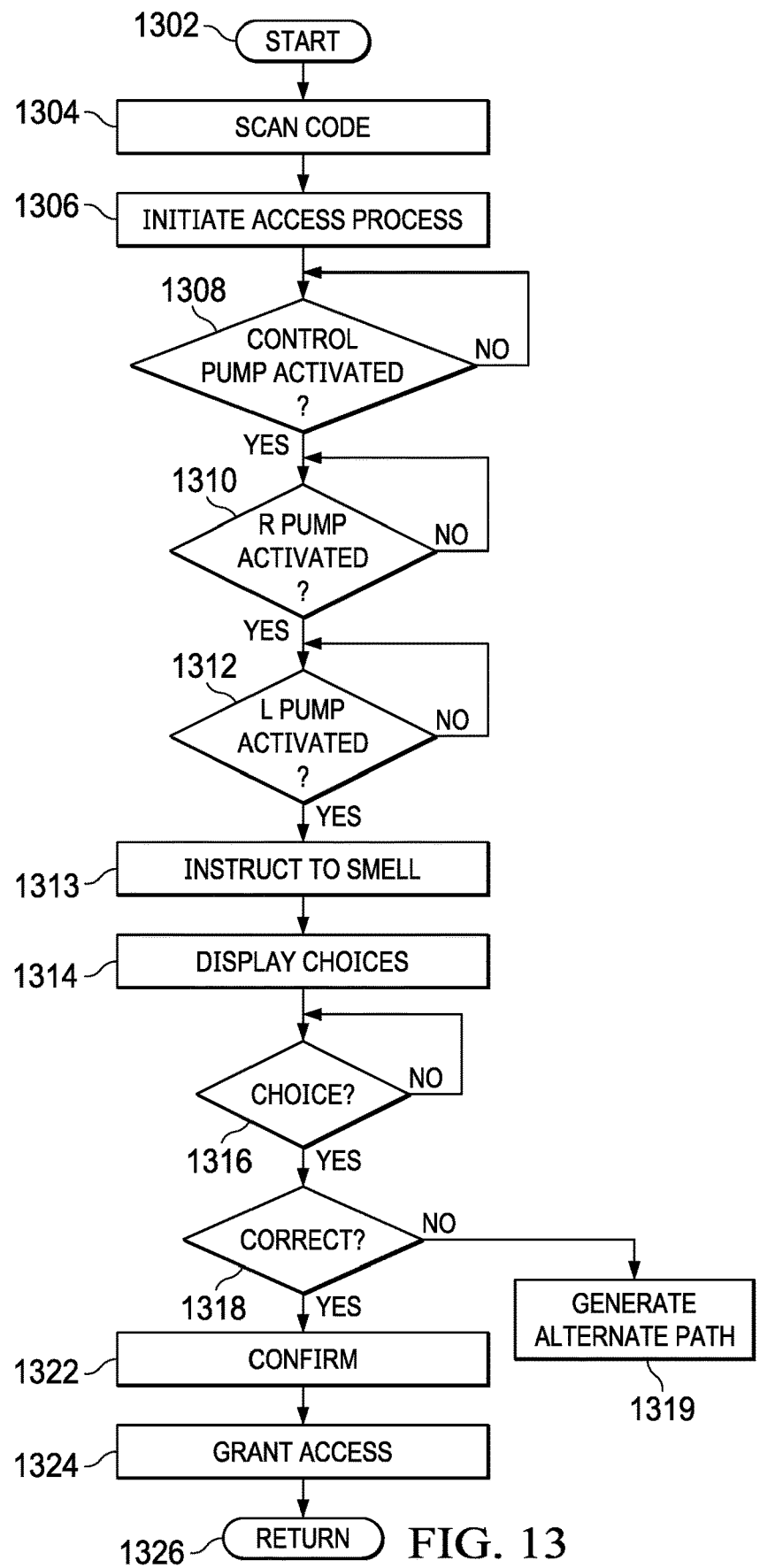
FIG. 13 illustrates a flowchart for one disclosed embodiment of the overall operation.

Referring now to FIG. 13, there is illustrated a flowchart for one disclosed embodiment of the overall operation. The program is initiated at a block 1302 and then proceeds to a block 1304 wherein the code is scanned from the ticket 207. The program then flows to a function block 1306 to initiate the overall access process. This, as described above, is in operation wherein the individual is given certain instruction such as removing any gloves or the such, and placing their hands underneath certain nozzles. The program then flows to a decision block 1308 to determine if the control pump is or has been activated and is ready to be operated. In this operation, it is possible that the individual is required to first place the right hand under the nozzle and then their left-hand under the nozzle. However, it could be that both are activated at the same time. The program then flows to a function block 1310 to determine if the right pump has been activated, this being for the right hand. The program then flows a decision block 1312 to determine if the left pump has been activated comes being for the left-hand. Once both pumps have been activated, the program flows to a function block 1313 in order to instruct the user how to proceed with smelling their hands. It can be an instruction to smell the right hand and then the left-hand or the opposite. The program then flows to a function block 1314 to display choices in a multiple-choice format. This display 909 is basically randomized, such that the correct choice is not always in the same location. In this operation, it is possible that the control could be distributed to either the right or the left hand or it could be that it is not the control antiseptic compound that is dispensed but, rather, two odorant-enhanced antiseptic compounds. The user is instructed in the function block 1313 to, after smelling your hands, make a choice on the touch display 909. Thus, the touch display 909 first displays instructions and then displays the choices. It could be that there is first displayed a first display for the left-hand and then a second display for the right hand, or both right hand left-hand choice displays could be displayed side-by-side at same time. It is noted that providing choices to the individual of actual odorants for a particular hand when in fact the control was dispensed actually introduces some controlled air into the system. This is a situation wherein you be seen that is or is not "guessing." Could be that both choices have a "none" choice. By having that show up randomly on the right or left hand choice, this can further validate the overall process.

Figure 14:
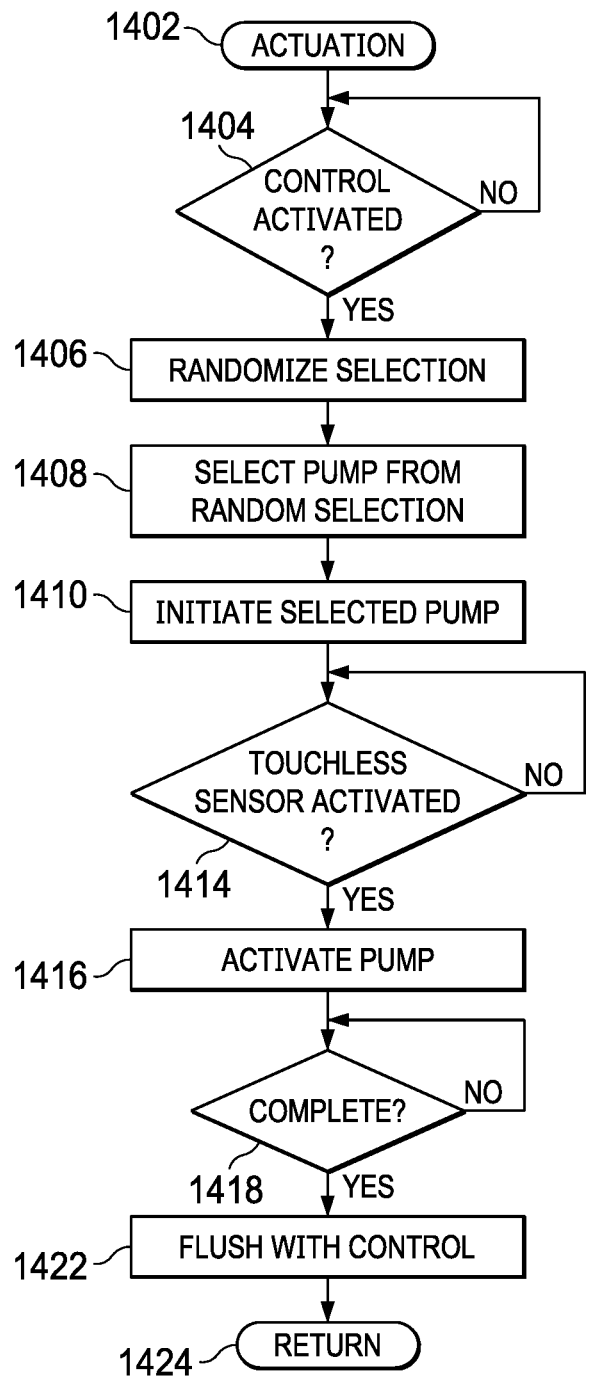
FIG. 14 illustrates a flowchart for an actuation process.

Referring now to FIG. 14, there is illustrated a flowchart for an actuation process. This is initiated at a block 1402 and then proceeds to a decision block 1404 to determine if the control path is activated. This is to be operated with a touchless system such that the pumps must first be activated or selected. Once the control antiseptic compound pump is activated or selected, the program flows to a function block 1406 wherein the selection of which of the odorant-enhanced antiseptic compounds is to be selected. The program then flows to a function block 1408 to select the pump from the resultant random selection. The program then flows to a function block 1410 to initiate the selected odorant-enhanced antiseptic compound pump to place it in a "ready" condition. The program then flows to a decision block 1414 to determine if a touchless sensor has been actuated for the overall dispensing operation. The program then flows to a function block 1416 to activate the respective pumps, i.e., control antiseptic compound pump and the selected odorant-enhanced antiseptic compound. The program then flows to a function block 1422, after the touchless sensor detects the removal of the hands from under the nozzle, to flush the nozzle associated with the odorant-enhanced antiseptic compound pump. The program then flows to a Return block 1424.

The program then flows to a decision block 1316 to wait for all of the choices to be made by the individual. Once made, the program flows to a decision block 1318 to determine if these choices are correct. Even if two odorant-enhanced antiseptic compounds are dispensed, it may be that only one need be detected and the correct choice made. If the correct choices are not made, the program flows to a function block 1319 in order to generate an alternate path of decision-making, i.e., subject the individual to a different test with different odorants. If correct, the program flows along a "Y" path to a function block 1322 in order to confirm the correct choice and then to a function block 1324 wherein access is granted, i.e., a gate is opened or an attendant is instructed to allow the individual to pass. The program then flows to a Return block 1326.

Figure 15:
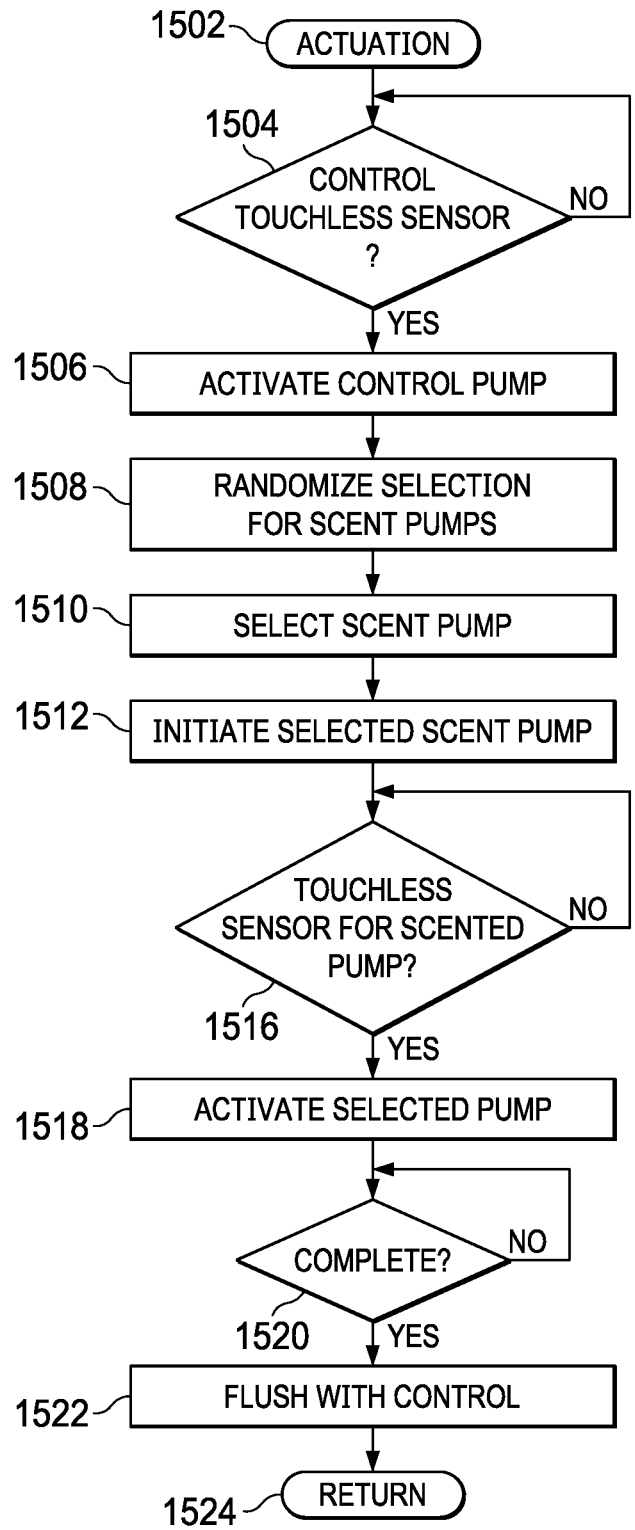
FIG. 15 illustrates a flowchart for an alternate actuation procedure.

Referring now to FIG. 15, there is illustrated a flowchart for an alternate actuation procedure, which is initiated at a block 1502. The program then flows to block 1504 to determine if the control touchless sensor has been activated. Once activated, the program flows to the function block 1506 to activate the control pump and then to a function block 1508 to randomize the selection for the odorant-enhanced antiseptic compound pumps and then to a function block 1510 to select the selected odorant-enhanced antiseptic compound pump for output. The program then flows to a function block 1512 to initiate the selected odorant-enhanced antiseptic compound pump and then to a decision block 1516 to determine if the touchless sensor for the odorant-enhanced antiseptic compound has been activated, i.e., the individual has placed their hand under the nozzle at the appropriate time. The program then flows to a function block 1518 to activate the selected odorant-enhanced antiseptic compound pump and then to decision block 1520 to determine when the operation is complete. This means that the individual has first placed their hand under the nozzle in a first operation to receive the dispensed control antiseptic compound and then the other hand under the same nozzle in a second operation to receive the dispensed odorant-enhanced antiseptic compound. Once the touchless sensor indicates that the hands have been removed from proximity to the novel, the operation is complete. The program then flows to a function block 1522 to flush the nozzle with the control antiseptic compound. The program then flows to a Return block 1524.

Figure 16:
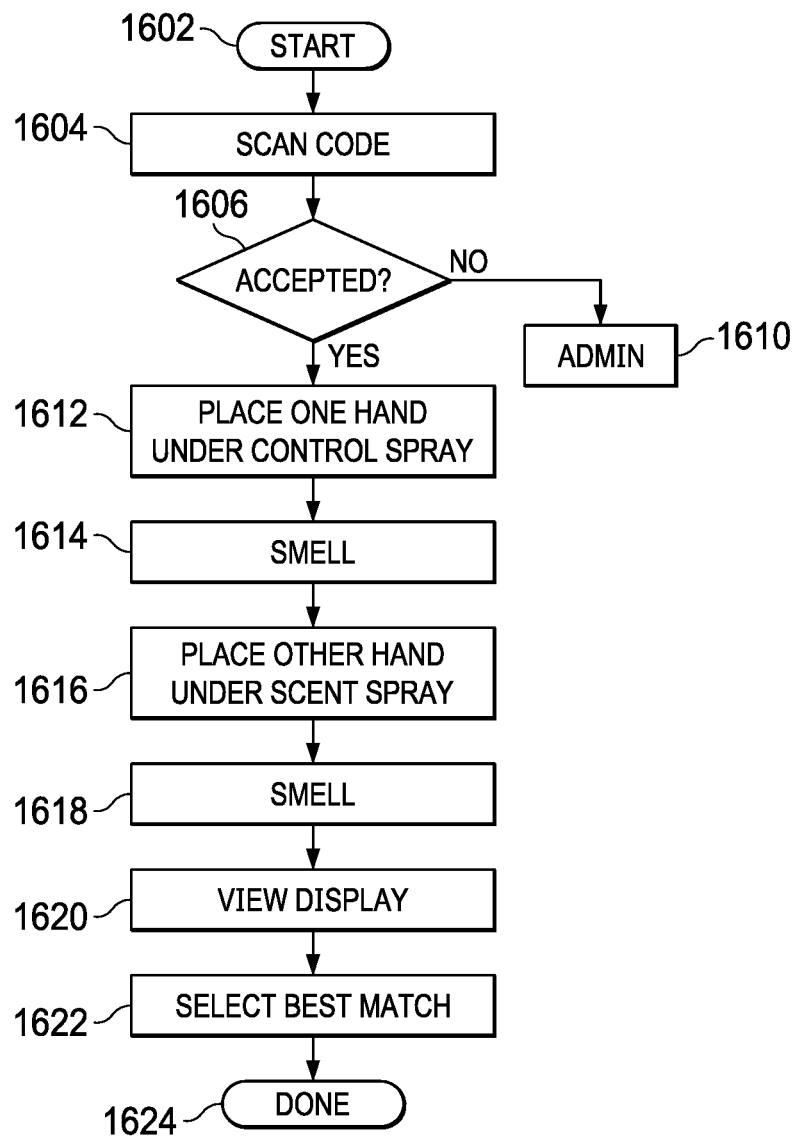
FIG. 16 illustrates a flowchart depicting a higher level view of the overall operation.

Referring now to FIG. 16, there is illustrated a flowchart depicting a higher level view of the overall operation, which is initiated at a block 1602. The program then flows to a function block 1604 in order to scan the code on the ticket 207. The program then flows to a decision block 1602 to determine if the scan code has been accepted by the system, i.e., it has been validated as an authorized ticket code for that particular venue or event. If not, the program flows along a "N" path to a function block 1610 to take administrative action. Once accepted, the program flows to a function block 1612 wherein one hand is placed under the control spray. The program then flows to a function block 1614 where the individual smells that hand. The program then flows to a function block 1616 to place the other hand under the odorant-enhanced antiseptic compound spray nozzle, noting that these could be the same nozzles. The program then flows to a function block 1618 wherein the individual is instructed to smell that hand. The program then flows to a function block 1620 wherein the individual views the display and into a function block 1622 to select the best match from the multiple-choice presentation. The program then flows to a Done block 1624. In this overall operation, the individual knows that one hand is a control hand and is important to smell at hand first and then smell the hand having the odorant associated there with.

Figures 17, 18:
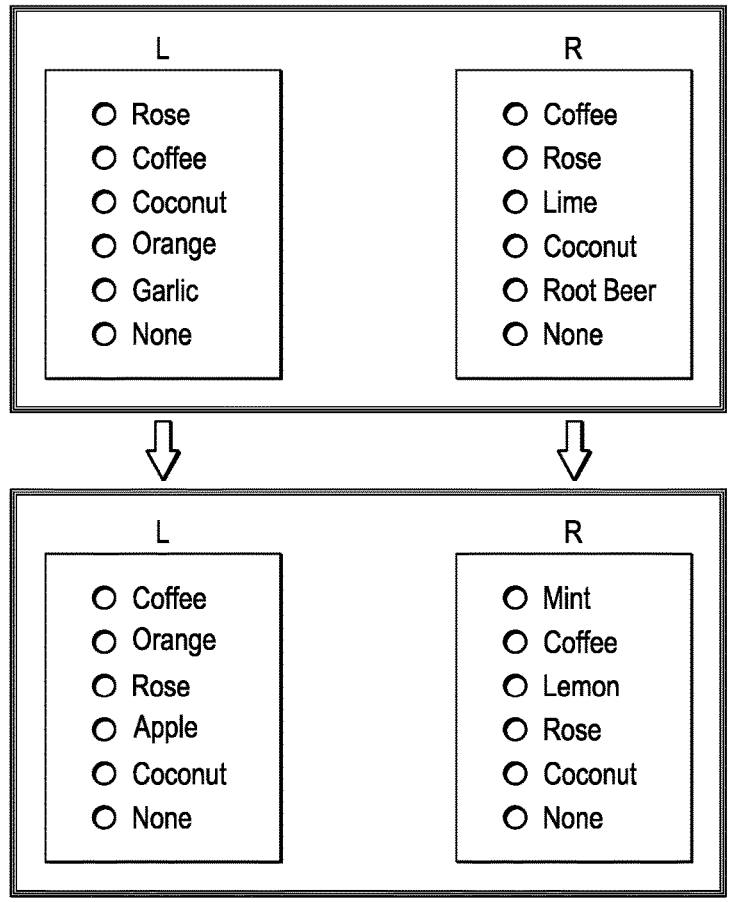
FIG. 17 illustrates two sequential displays that are presented to two different individuals.
FIG. 18 displays a layout of a relational database.

Referring now to FIG. 17, there illustrated two sequential displays that are presented to two different individuals. It can be seen that the upper box represents a first instance of time wherein a displays provider for the left-hand and the right-hand. It could be that either of these hand has been associated with a dispensed control antiseptic compound or both have been associated with a dispensed odorant-enhanced antiseptic compound. Even though only, in one example, there are 5 available odorant-hands in a septic compounds, they can be that other odorants are displayed. It can be seen in the bottom pane, for the next display that different choices are present. These are randomize such that, for example, if a coconut scent were dispensed, it would appear at different positions.

Referring now to FIG. 18, there is displayed the layout of a relational database. This relational database is all keyed to the ID, i.e., the unique barcode number on the ticket 207. There are provided columns as to what scent was dispensed in the control nozzle and the scent nozzle. And his example, only one nozzle was associated with odorant-enhanced antiseptic compound and the other associated with a control antiseptic compound. However, it could be that the control nozzle could have had odorant-enhanced antiseptic compound dispensed therefrom. There is a Result column indicating whether the particular ID was associated with a correct result, i.e., did they indicate the correct scent. There is also a date and time column indicating when the particular test was carried out.

Figure 19:
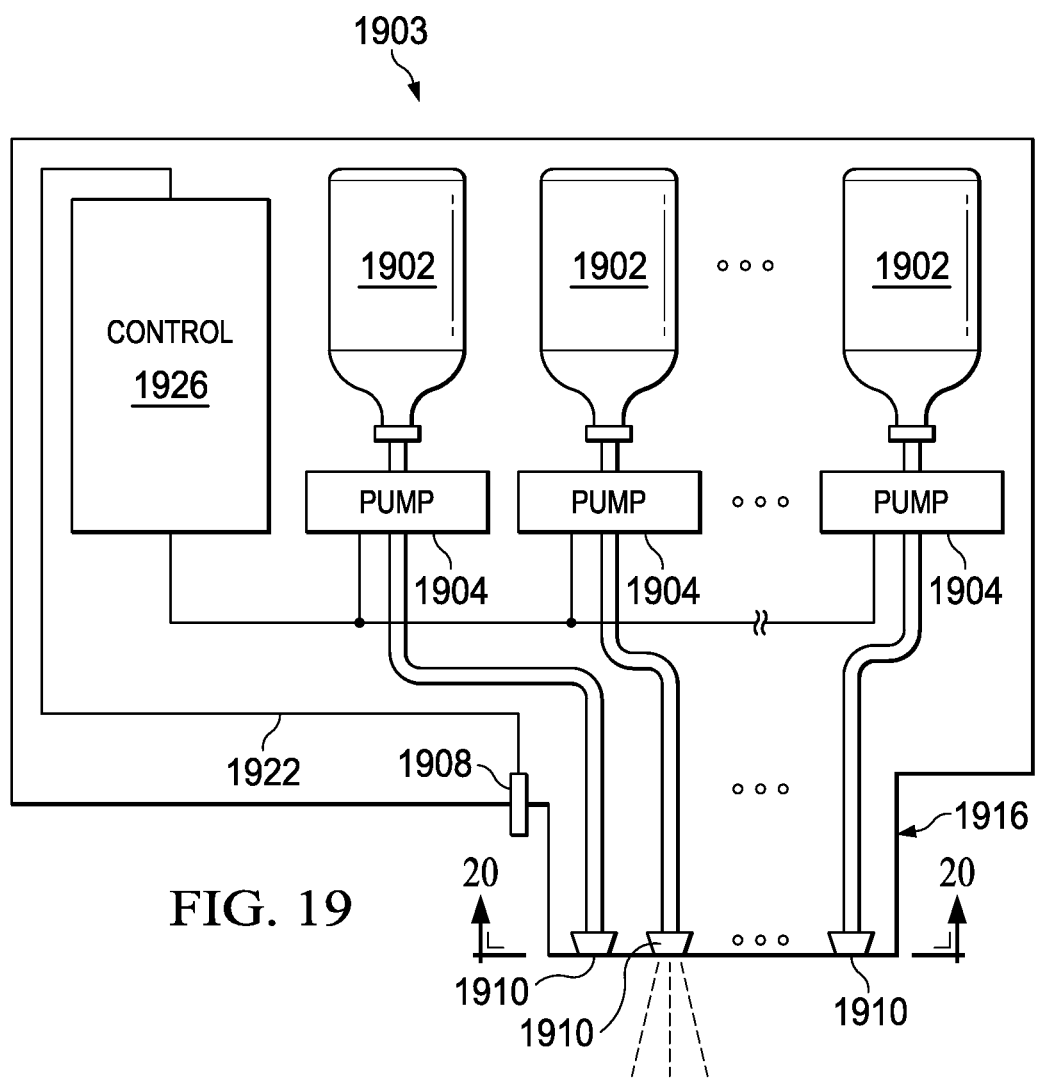
FIGS. 19 and 20 illustrate an alternate antiseptic compound dispenser.
Figure 20:
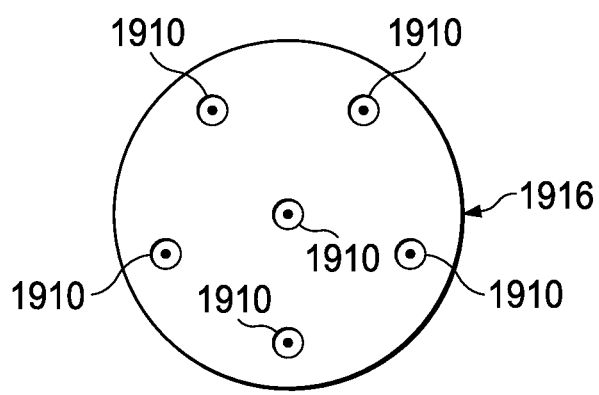

Referring now to FIG. 19, there is illustrated the diagrammatic view of an alternate antiseptic compound dispenser 1903, wherein there is provided a single outlet 1916 for multiple nozzles 1910. There are contained within the dispenser 1903 a plurality of reservoirs 1902, each containing either a control antiseptic compound or odorant-enhanced antiseptic compounds. Each of these reservoirs 1902 has a pump 1904 associated there with, which is controlled by a control block 1920, this control box 1920 associated with the local PC 902. There is provided a touchless sensor 1908 they sense line 1922 that goes back to the control block 1920. Thus, by the individual holding their hand under the outlet 1916 and it being sensed by the touchless sensor 1908, any one of the pumps 1904 can be activated, depending upon the sequence described hereinabove. A detail of the nozzles 1910 as they are disposed in the outlet 1916 is illustrated FIG. 20. It can be seen that these nozzles 1910 are clustered in a group. It may be that the center most nozzle 1910 is associated with the control antiseptic compound.

The issues associated with a lack of smell may also be tested using self-test systems for identifying diseases such as COVID 19 for a patient or controlling access to various types of locations through a controlled portal. Smell disfunction can be used as an indication of a wide variety of disease states. While most common causes of smell disturbance relate to nasal or sinus diseases, upper respiratory infections and head traumas, frequent causes of smell disturbance include oral infections, oral appliances, dental procedures and Bell's Palsy. Medications can interfere with a smell and taste and should be reviewed in all patients reporting a nasal dysfunction. Convincing evidence indicates that olfaction is impaired in a variety of neurodegenerative disorders. Examples of these common diseases include Parkinson's disease, Alzheimer's disease, and dementia with Lewy bodies. Olfaction is lost in the majority of the patients affected by these conditions.

Figure 21:
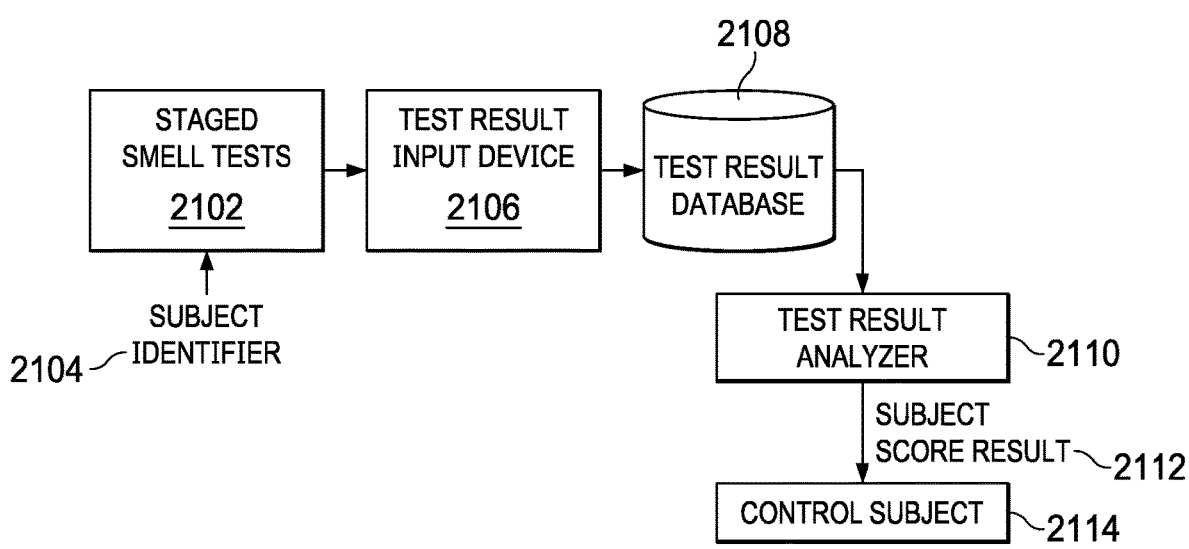
FIG. 21 illustrates a staged approach for self-testing a sense of smell of an individual.

Referring now to FIG. 21, there is illustrated a manner for providing a staged approach to enable individuals to self-test their sense of smell and be scored for accuracy. An individual receives a set of staged smell tests 2102 that provide multiple tests in a staged sequence with respect to the individual's ability to smell certain fragrances as described above. Each of the tests are associated with a unique subject identifier 2104 that associates a particular test with a specific individual. The results of each of the staged tests are provided to a test result input device 2106 to record the user's reaction to a particular smell. The test result input device 2106 may comprise a mobile device application or interactive display associated with the test dispenser that enables a user to enter answer questions regarding the smell detected when taking the smell test using either touchscreen displays or voice recognition technologies. The test result input device 2106 may comprise any apparatus capable of noting a subject's answers to the test be taken.

The test results are stored within a relational database 2108. The database 2108 comprises a relational database that associates the test results for each of the staged tests with the provided subject identifier 2104 associated with the individual taking the test. The test results stored within the test results database 2108 are provided to a test results analyzer 2110. The test results analyzer 2110 determines a score associated with the individual taking the test based upon whether the correct smells have been detected using the staged test results. Based upon the test results, an individual score can be manually or electronically computed to determine a real time screen of a variety of possible disease states. The analyzer 2110 provides a subject score result 2112 based upon the results of the tests. The subject's result 2112 can be used by the individual or an entity conducting the chemo sensory disorder test in order to direct the individual to additional testing services or options. The entity testing the individual can use the result as a possible indicator that the tested individual may infect or expose other individuals within the immediate vicinity and approve or deny access to particular locations. The subject score result 2112 is used to control the subject 2114 in a desired manner. The score 2112 may be used to direct individuals to other locations, direct individuals to medical authorities, direct individuals to self-quarantine and to direct individuals to have additional health screening tests performed.

Figure 22:
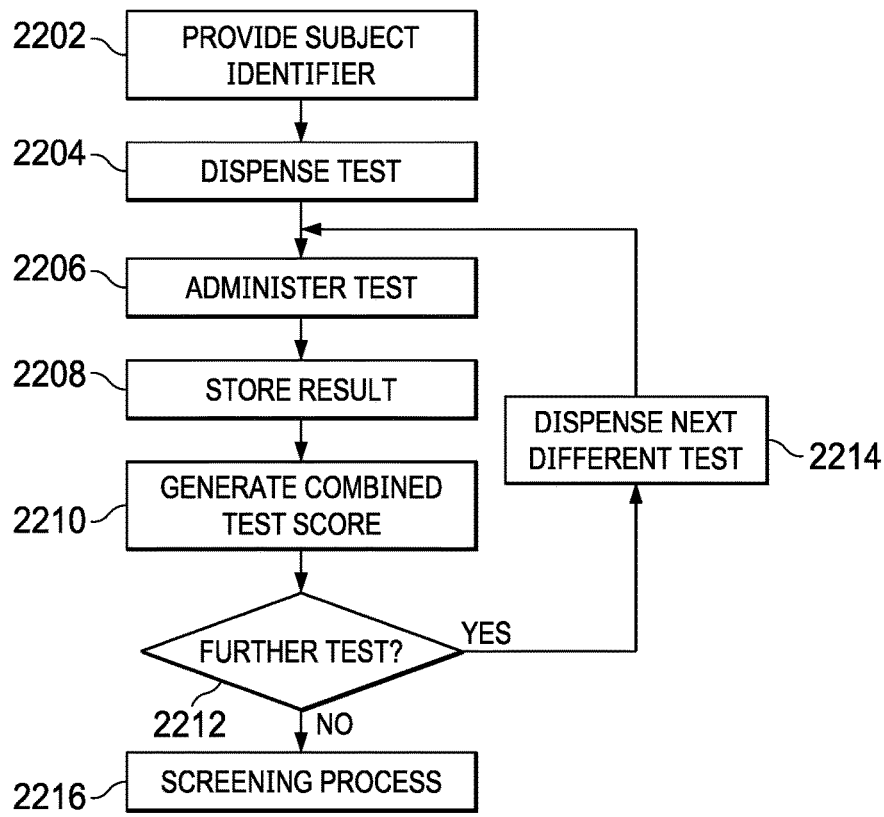
FIG. 22 illustrates a flow diagram for providing staged self-testing for a loss of a sense of smell of an individual.

Referring now to FIG. 22, there is illustrated a flow diagram of the process for providing staged self-testing of individuals to detect loss of sense of a smell. Initially, an individual desiring to be self-tested provides at step 2202 a unique subject identifier at a scanning station. The identifier may comprise a barcode, QR code, magnetic card stripe, chip identifier, or any other means for uniquely identifying an individual. The codes may for example be placed upon tickets or other coupons used for accessing a particular venue. The magnetic card stripes or chip identifiers may be utilized on drivers licenses, student IDs, work IDs or any other type of card or badge necessary to enable an individual access to a particular area or to identify the individual in a unique fashion. Once the subject identifier has been provided at step 2202, the test is dispensed at step 2204. The dispensed test may be the application of a spray or gel onto the hand or hands of a user as more particularly described hereinabove particularly with respect to FIG. 19. Additionally, the dispenser could dispense packets including a cloth or wipe therein that provides a fragrance for testing the individual's sense of smell. It should be realized by one skilled in the art that any manner for providing a fragrance for smelling by a test subject may be utilized. Next, the test is administered by the individual at step 2206. Administration of the test requires the individual to smell the fragrance provided by the spray, gel, cloth, etc. and enter an indication of the smell that they detected through an associated display interface or mobile device application interface associated with the self-testing process.

The results of the test are stored in a relational database at step 2208. The stored test results are used for the creation of a combined test score at step 2210. The combined test store utilizes each of the staged tests that have been conducted thus far to provide a combined score based on each of the provided test. Thus, if only a single test has currently been provided, the combined score would comprise the results of that single test. If multiple tests have been conducted then whether or not the user had passed or failed a predetermined number of smell test is used for determining the combined score. Inquiry step 2212 determines if there are further tests to be conducted in the staged test process. If so, the next test that is different from previously provided tests is dispensed at step 2214. The dispensing of the test would occur in a similar manner to that occurring in step 2204 and may comprise spraying or squirting a spray or gel onto the hands of the user as described more fully hereinabove or utilizing a cloth or other material having a fragrance embedded therein within a provided packet. If inquiry step 2212 determines that no further tests are to be utilized, control passes to the screening process 2216 for determination on treatment of the individual based upon the combined test score. Screening may involve allowing or not allowing entry of an individual into a particular location, designating the individual for further screenings, directing the individual to medical professionals for further screenings, or directing the individuals to self-quarantine.

Figure 23:
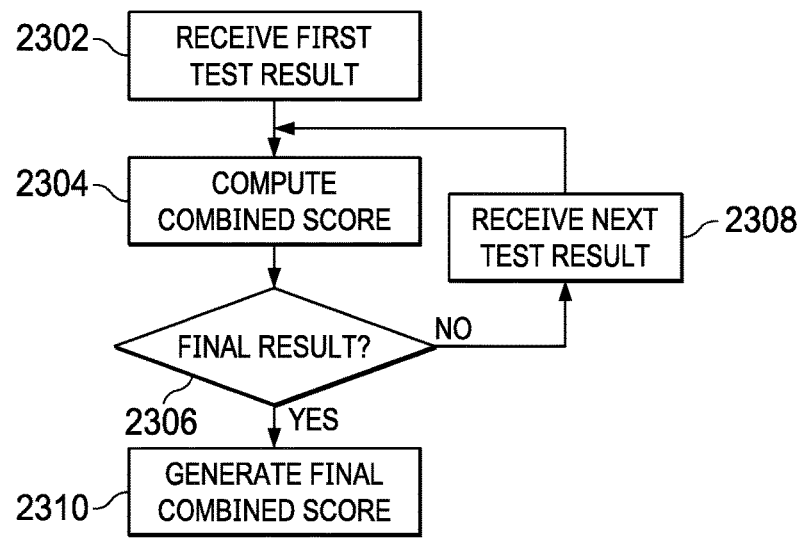
FIG. 23 illustrates a flow diagram describing a process for generating a combined score for a smell test.

Referring now to FIG. 23, there is more particularly illustrated the process for generating the combined score of step 2210 discussed above. A first test result is received at step 2302. The received test result is used to compute a combined score at step 2304. The computation of the combined score will be based upon the number of test results that have been currently receive. Thus, if only the first test result has been received, the combined score is based upon one test result. Subsequent to the first test result, the combined score will be updated based upon the results received from subsequent test results as will be described herein below. Inquiry step 2306 determines if the final test result has been received from the stage testing process. If not, control passes to step 2308 and the next test result is received. Control passes back to step 2304 to determine the new combined score based upon the newly received test result. Once all of the test results have been received a final combined score is output based upon the previously computed combined score and the new result at step 2310. This final combined score may be used for enabling access to a facility or directing the subject to further testing protocols as described hereinabove.

While many of the discussions hereinabove have been made with respect to utilizing smell test to detect the potential presence of the COVID 19 virus, as further mentioned various types of smell tests may be used as a chemo sensory disorder test for any number of potential issues. The chemosensory disorder test may be offered in a variety of forms. These include the multi-dispenser or single dispenser controlled system described hereinabove with respect to providing access to a ticketed venue, individual color-coded packages, individual machine-readable coded packages, individual mechanical sprays, individual manually applied lotions or liquids, individual "scent embedded" media such as paper products and individually inhaled olfaction dispensers. Any or all of these various techniques may be used to administer a test to an individual.

Figure 24:
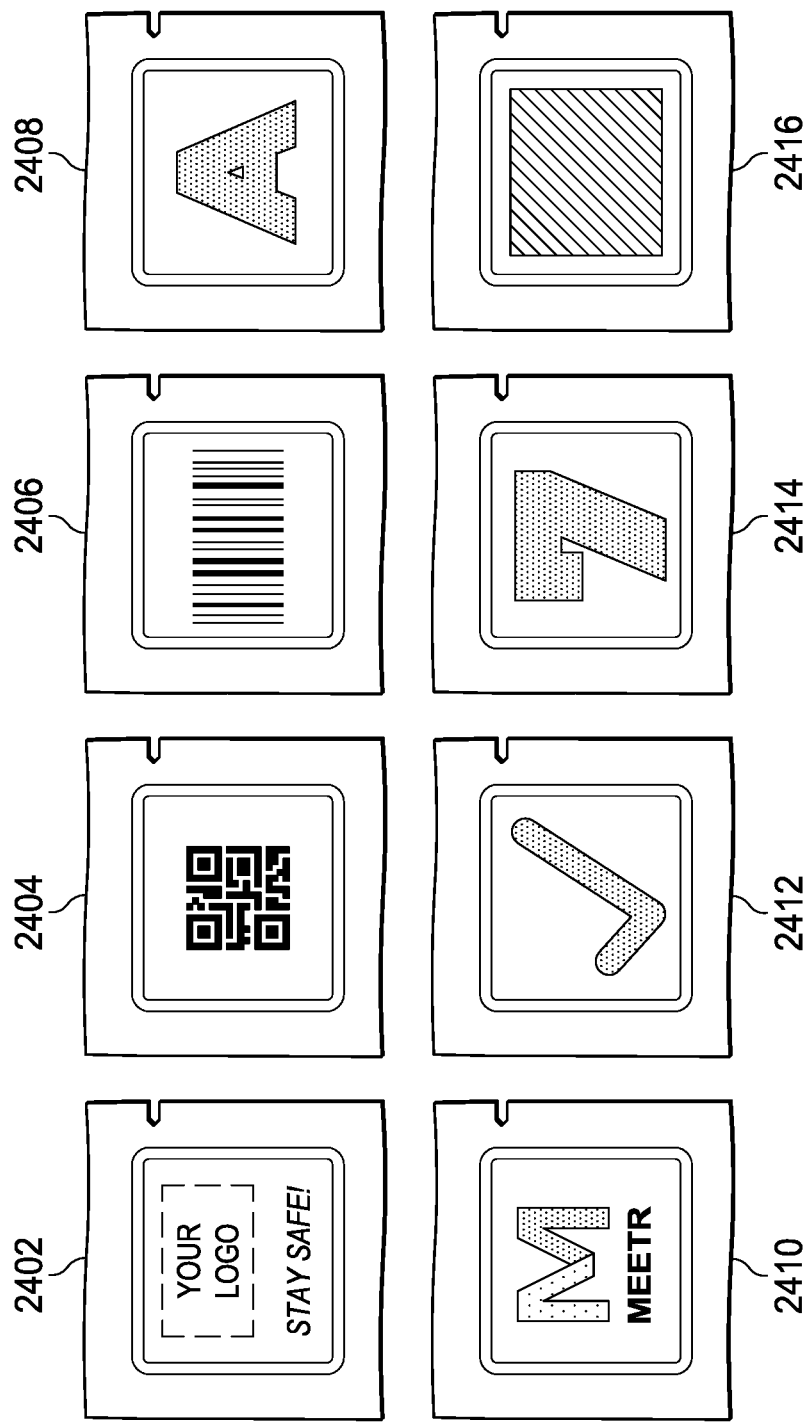
FIG. 24 illustrates various code identifiers that may be used with packets containing a scented material.

Referring now more particularly to FIG. 24, if a packet test is used for detecting an individual sense of smell, the packets can be coded in a variety of fashions that enable the system to know the particular smell associated with the packet without providing the test-taker any hint as to the smell associated with the packet. Individual packages would allow for each scent to be visually identified as the "scent markers" within the packets by means of a particular business logo 2402, a machine readable QR code 2404 or a machine-readable barcode 2406. Other types of packages identifiers include letter indications 2408, symbol indications 2412, number indications 2414 and color indications 2416. Each of the particular coded indications are associated with a particular smell. Thus, a coconut smell could be associated with the color blue, number eight, a checkmark symbol, the letter "A" or a bar or QR code. Thus, when the test results with respect to the particular packet were entered, the user would enter the particular code on the face of the packet and then indicate what smell they detected. The testing system would record whether the subject had accurately indicated the smell associated with the entered packet code. The packaging code upon the packets would have no visible means of identifying the smell contained therein. For example, a lemon smell would not be included in a packet with a yellow color code on the packet. Alternatively, the packets could include a combination of unique symbols, brand IDs, alphabetic indicators and numeric indicator combinations to provide the unique test code indication. The codes could also include unique symbology associated with the specific place where the test are being administered such as sports teams, sports leagues, players and the like.

Figure 25:
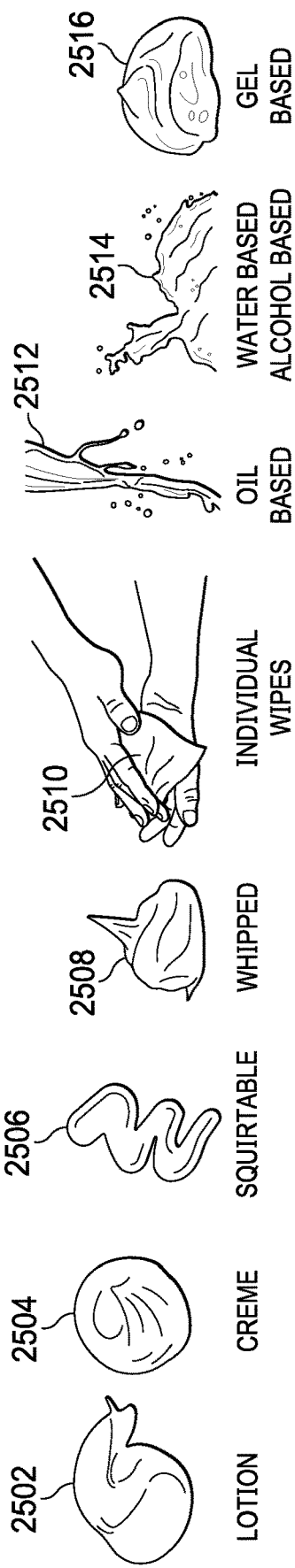
FIG. 25 illustrates various mediums for containing a testing scent.

As discussed previously, the manner for administering the smell test fragrance in addition to using the above described packets may utilize the multi-fragrance dispenser within a sanitizer such as that described hereinabove with respect to FIG. 19. Alternatively, the system could dispense individual packets providing a predetermined smell. Referring now to FIG. 25, there are illustrated the various testing mediums and into which fragrances may be embedded to provide the chemosensory disorder testing to test subjects. Testing mediums include a lotion 2502, a cream 2504, a squirtable media 2506, a whipped media 2508, individual wipes 2510, oil-based media 2512, water or alcohol-based media 2514 and gel based media 2516. The chemosensory disorder testing medium provides a dual function when providing the testing fragrance combined with a hand sanitizer.

Hand sanitizer, also called hand antiseptic, or hand rub comprises an agent applied to the hands for the purpose of removing common pathogens (disease-causing organisms). Hand sanitizers typically come in gel or liquid form. The use of hand sanitizer is recommended when soap and water are not available for handwashing or when repeated handwashing compromises the natural skin barrier (e.g., causing scaling or fishers to develop in the skin). Depending on the active ingredient used, hand sanitizers can be classified as one of two types: alcohol-based or alcohol free. Alcohol-based products typically contain between 60-95% alcohol, usually in the form of ethanol, isopropanol or n-propanol.

Figure 26:
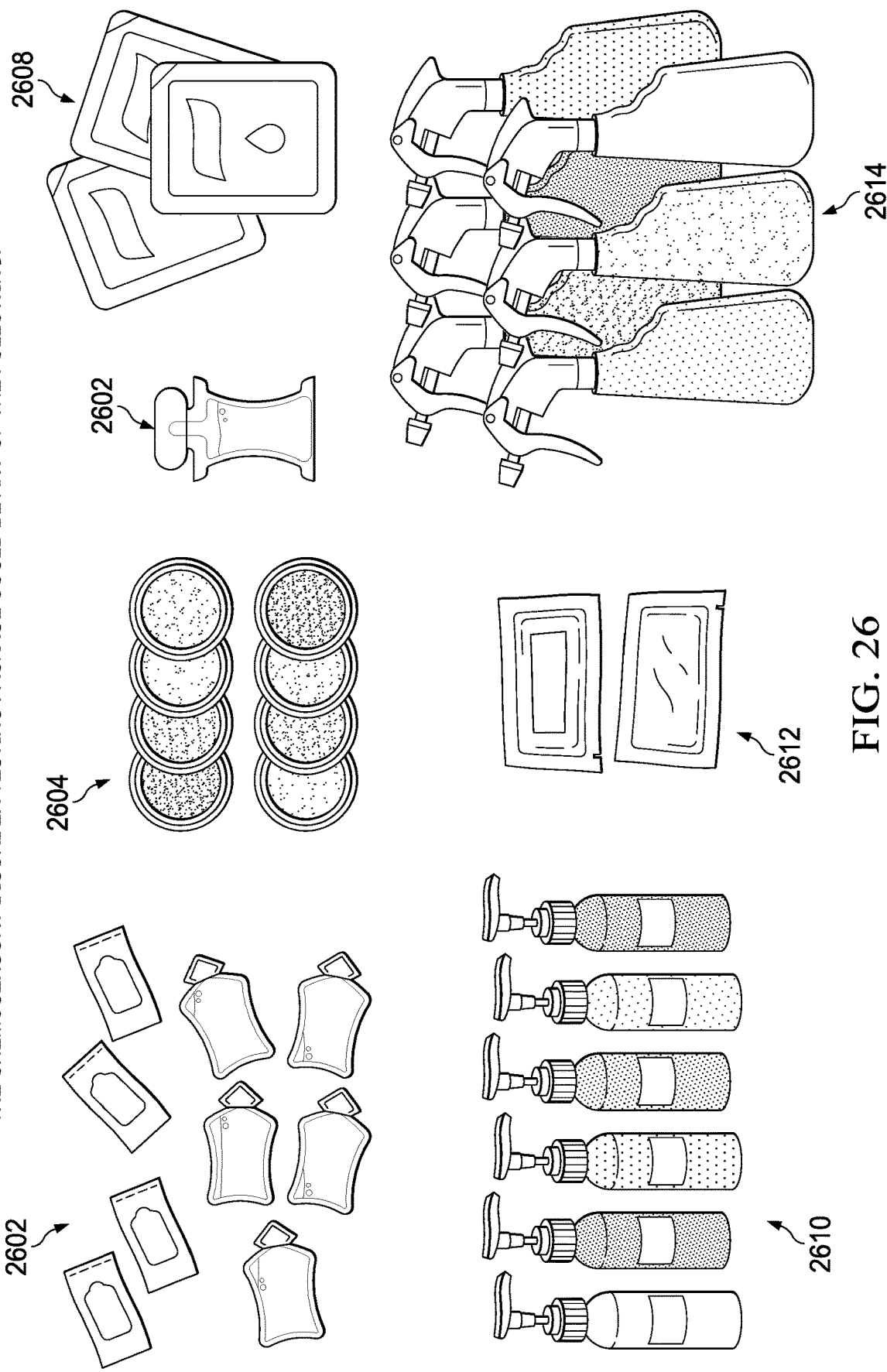
FIG. 26 illustrates various manners for packaging smell test mediums.

Referring now to FIG. 26 there are illustrated many different types of packaging which may be utilized for containing the testing medium. These include individual disposable plastic packets 2602, fragrance multicolored infused disks 2604, individual packets including peel off lids 2608, multicolored small pump bottles 2610, individual packets 2612 and multicolored spray bottles 2614. Any packaging that may contain a fragrance infused medium may be utilized to enable application of the medium to a user or presentation of the fragrance associated with the medium to a test subject's nose. The packaging may also be color coded to indicate the particular fragrance that is being dispensed by the packaged unit.

Figure 27:
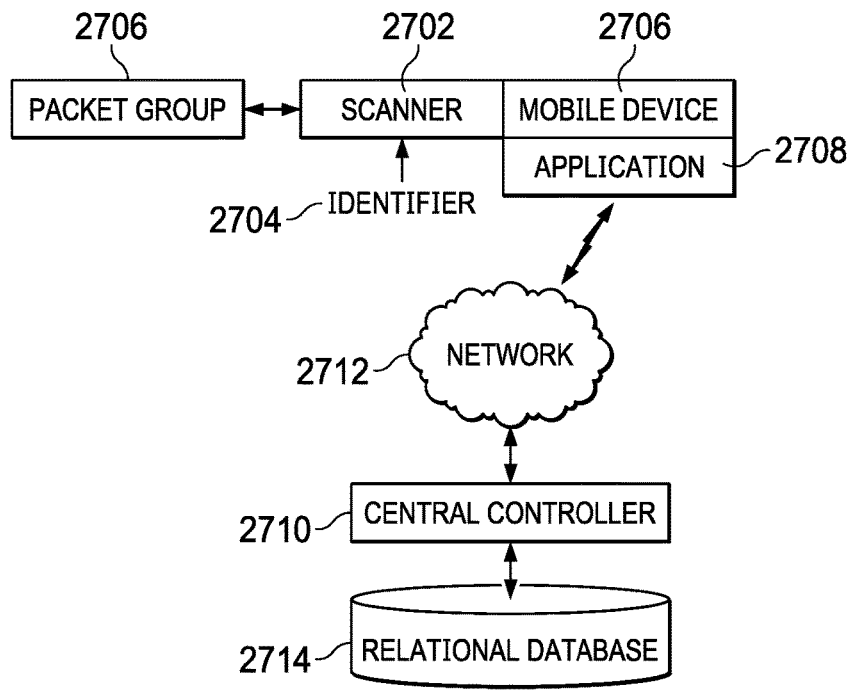
FIG. 27 illustrates a block diagram of a first embodiment of a system utilizing packets for enabling individual self-testing for chemosensory disorders.
Figure 28:
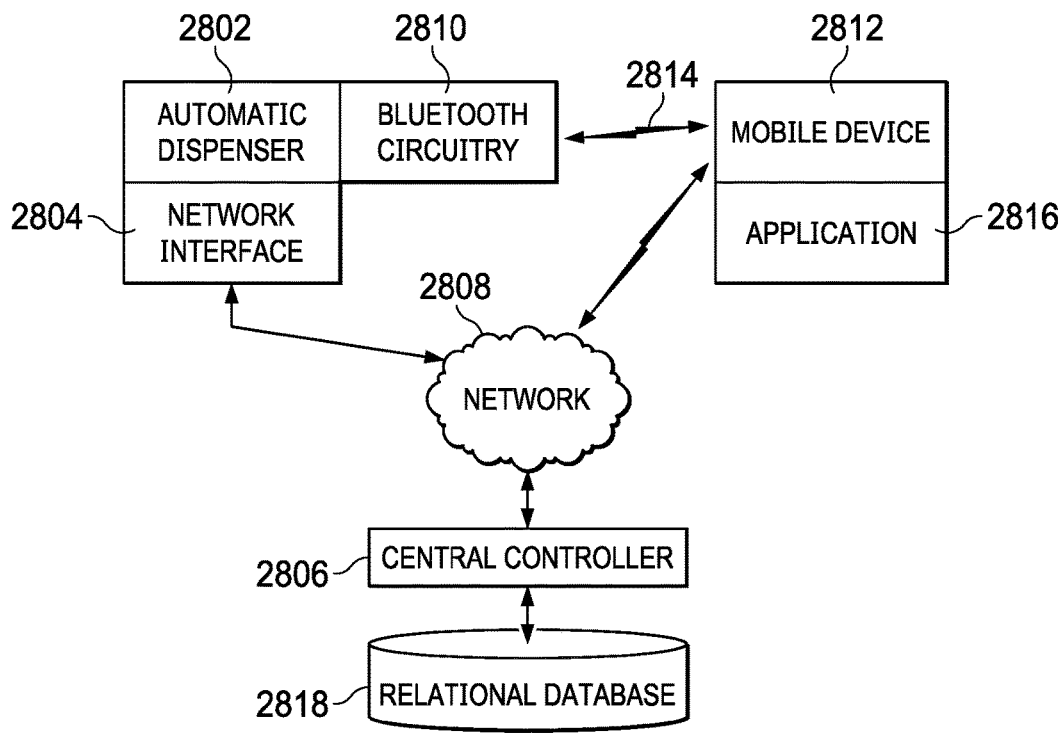
FIG. 28 illustrates a block diagram of a second embodiment of a system using an automated spray dispenser for enabling individual self-testing for chemosensory disorders.

Referring now to FIGS. 27 and 28 there are provided block diagrams of systems for enabling an individual to self-test using chemosensory disorder testing technology in order to determine if additional processes with respect to the individual are necessary. Individuals may be manually sprayed, tested and the test results recorded via a human interface and interaction. Interactions may also be digitally managed as shown in FIGS. 27 and 28 with both spray and testing utilizing touchscreens, electronic dispensers, tablets and mobile devices. Individuals can walk up to staged dispensers and self test and report what they smell on an item basis to provide a self-testing process.

FIG. 27 illustrates a system that utilizes packets for the self-testing process. A scanner 2702 scans an identifier 2704 that is associated with a particular user or item. The identifier can be barcodes on a ticket or coupon possessed by an individual or may be some type of identification including a magnetic strip or chip included on a license, ID card, credit card etc. that is specific to a particular individual. A further identifier may also be provided by the particular testing station that is providing the test to the user. This testing station identifier can also be associated with the test results and stored in the database as described below. The scanner 2702 can also scan identifiers associated with a particular packet group 2706. The identifiers associated with the packet group 2706 may comprise any of the bar codes, QR codes, colors, numeric identifiers, alphabetic identifiers, etc. that were discussed previously. The scanner 2702 may be associated with a mobile device 2706 such as a mobile telephone, tablet, laptop computer, etc. that includes the processing capabilities necessary for performing the chemosensory disorder testing functionalities. An application 2708 enables the mobile device 2706 to communicate information regarding the test identifier of the packet group 2706 and the individual identifier 2704 to a central controller 2710 over a network such as the Internet 2712. The central controller 2710 stores the self-test information within a relational database 2714 where the test result information is stored with respect to the identifier 2704 for the individual taking the test.

Thus, upon accessing the self-testing system an individual utilizes their mobile device 2706 to scan the identifier 2704 on a ticket or other identifier associated with the individual. The individual selects a packet 2706 for testing and smell the material within the packet in order to take the test. The individual scans the identifier associated with the packet 2706 and enters information through an application 2708 within the mobile device 2706 indicating the smell detected by the individual from the material in the packet. The results of this test result entered by the user is transmitted from the mobile device 2706 to the central controller 2710 over the network such as the Internet 2712. Finally, the test result information is stored within the relational database 2714 with respect to the individual identifier 2704 that was provided.

Referring now to FIG. 28, there is illustrated an alternative embodiment of a system for providing a chemosensory disorder test using an automatic dispenser 2802 rather than packets. The automatic dispenser 2802 includes a network interface 2804 that enables the automatic dispenser 2802 to communicate with a central controller 2806 over a network of 2808 such as the Internet. The automatic dispenser 2802 may comprise for example the configuration described herein above for dispensing a spray onto the hand of the user in FIG. 19. The dispenser 2802 could dispense a single or multiple fragrances onto the hands of the user in accordance with the techniques described above. The automatic dispenser 2802 also includes Bluetooth circuitry 2810 enabling communications with mobile devices 2812 over a Bluetooth communications link 2814. The mobile device 2824 includes a mobile application 2816 thereon enabling the entry of information that can be provided to the central controller 2806 over a communications link through the Internet 2808. The application 2816 is used to provide the user identifier, the test identifiers associated with the test provided by the automatic dispenser 2802, and receive the test results entered by the user responsive to smelling a fragrance dispensed by the automatic dispenser 2802. These test results are transmitted from the mobile device 2812 to the central controller 2806 over the Internet network 2808 and stored within a relational database 2818 such that the test results are associated with a particular identifier associated with the user providing the test results.

When utilizing the system of FIG. 28, an individual utilizes their mobile device 2812 to start the app 2816 and provide a user specific identifier. The app 2816 requests that the automatic dispenser 2802 dispense a scent for testing and provides this request to the central controller 2806. The central controller 2806 controls the automatic dispenser 2802 to dispense a particular fragrance that the user would smell. The user identifies the detected smell through the app 2816 on their mobile device 2812 from multiple choices and this test result are forwarded back to the central controller 2806 for storage within the relational database 2816. The central controller 2816 is able to indicate whether the appropriate smell was detected since the central controller 2806 controls the particular scent that was dispensed by the automatic dispenser 2802. The central controller 2806 stores the test result indicating whether the user had passed or failed within the relational database 2816 associated with the identifier for the user.

Figure 29:
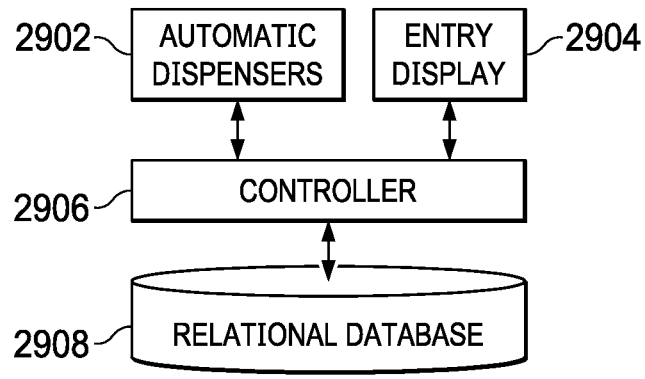
FIG. 29 illustrates an automated dispenser with associated entry display.

The testing process for performing a user self-test of a chemosensory disorder is further illustrated in FIG. 29. FIG. 29 illustrates an automatic dispenser 2902 having an associated entry display 2904. The entry display 2904 allows an individual being tested to enter their responses to fragrances detected by the individual that have been dispensed by the automatic dispenser 2902. The aromatic dispenser 2902 may have a similar configuration to those described herein above for dispensing a known scent within a hand sanitizer or other dispensable material that is under the control of the dispenser 2902 responsive to instructions received from a controller 2906. The controller 2906 controls the operation of the automatic dispenser 2902 and enables the outputting of known fragrances that may be compared with the responses entered by the user through the entry display 2904 in order to determine whether an individual has passed or failed the chemosensory disorder test. The results of the test along with an identifier associated with the user that has been entered through the entry display 2904 are stored in a relational database 2908. The database 2908 includes an indication of the identifier of the particular user and the result of the test or tests that are associated with the user.

Figure 30A:
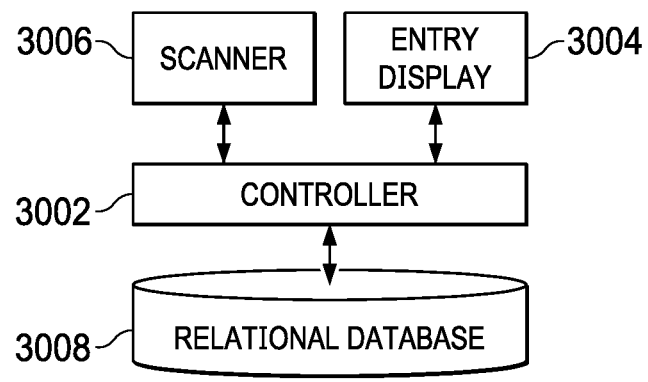
FIG. 30A illustrates a user self-test station using packets for a testing process.

Referring now also to FIG. 30A, there is illustrated a user self-test station wherein packets are used for the testing process rather than the automatic dispenser such as that described above. This configuration also includes a controller 3002 that receives inputs from an entry display 3004. However, rather than controlling an automatic dispenser, the controller 3002 is integrated with a scanner 3006. The scanner 3006 would scan a code associated with a test that is included on the face of a packet containing the fragrance used for the test. Thus, an individual would select a packet from a bin associated with the self-testing station and hold the printed code on the packet up to a scanning mechanism. Various types of codes can be used as described hereinabove. The scanner 3006 what identify the code and provide this information to the controller 3002 such that the controller was aware of the test being provided. The controller 3002 compares the expected test result with the test response entered by the user via the entry display 3004. The controller 3002 stores the test result within a database 3008 at a location associated with a unique user identifier that has also been provided either via the entry display 3004 or the scanner 3006.

Figure 30B:
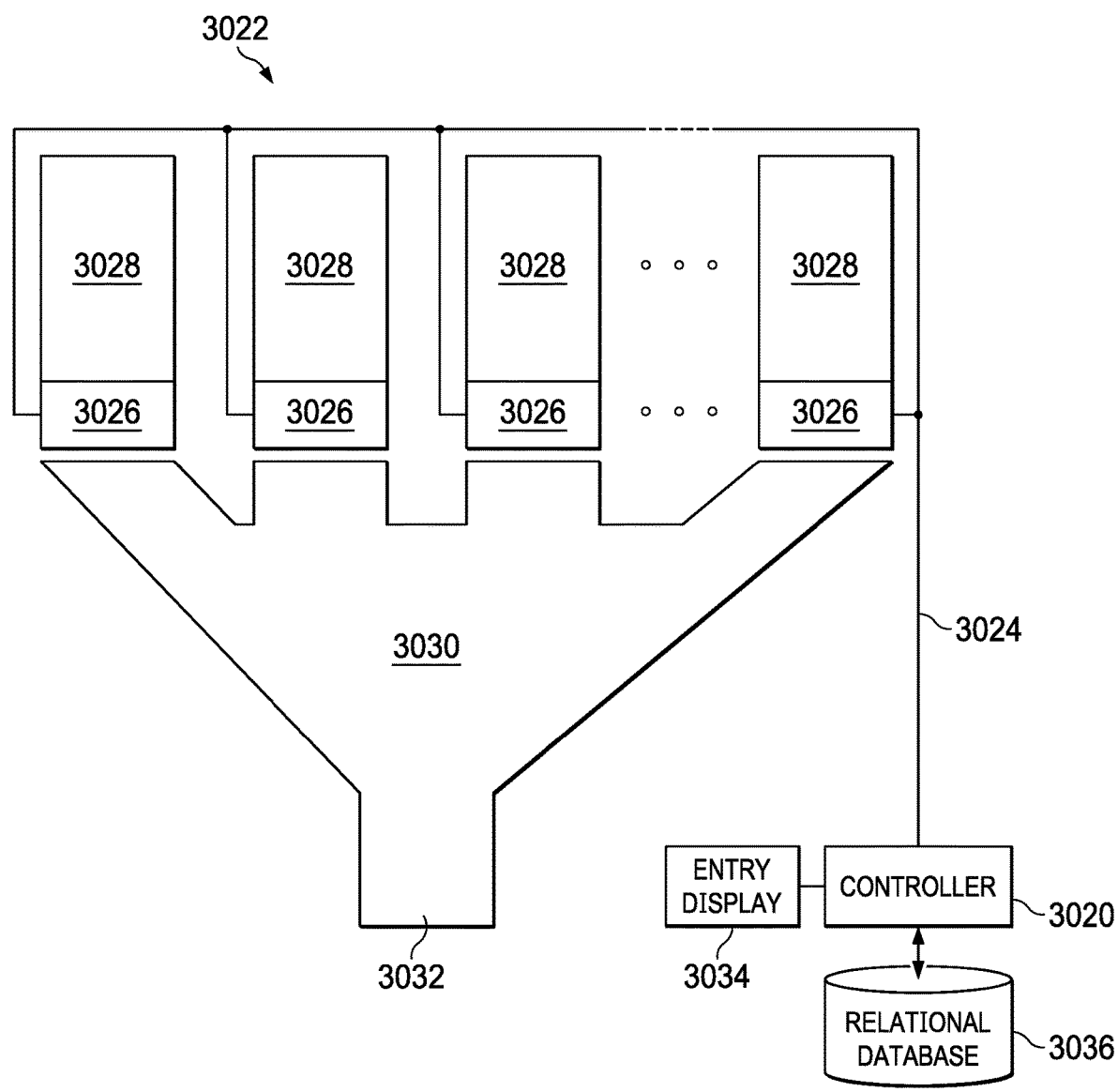
FIG. 30B illustrates a more detailed block diagram of a packet dispenser system.

FIG. 30B more particularly illustrates an embodiment of the system wherein rather than packets being drawn by the individual and scanned are automatically dispensed under the control of the central controller 3020 through a controlled feed mechanism 3022. The central controller 3020 provides control signals via control line 3024 to an access control mechanism 3026 to provide a single known packet to the individual being tested response to receiving a request to a self-test from an application on a mobile device or other actuation mechanism. A series of bins 3028 are provided wherein each of the bins contains a separate group of packets containing a single fragrance. When the access control mechanism 3026 receives a signal via the control line 3024, a single packet is dispensed from the associated bin 3028. The dispensed packet then travels down a chute 3030 to be dispensed to the user at an outlet 3032. The user will open the packet and utilize the wipe or cloth contained therein to attempt to detect the smell and provide an indication of the smell they detected through the entry display 3034. This result is provided back to the controller 3020 and entered into the relational database 3036.

Figure 31:
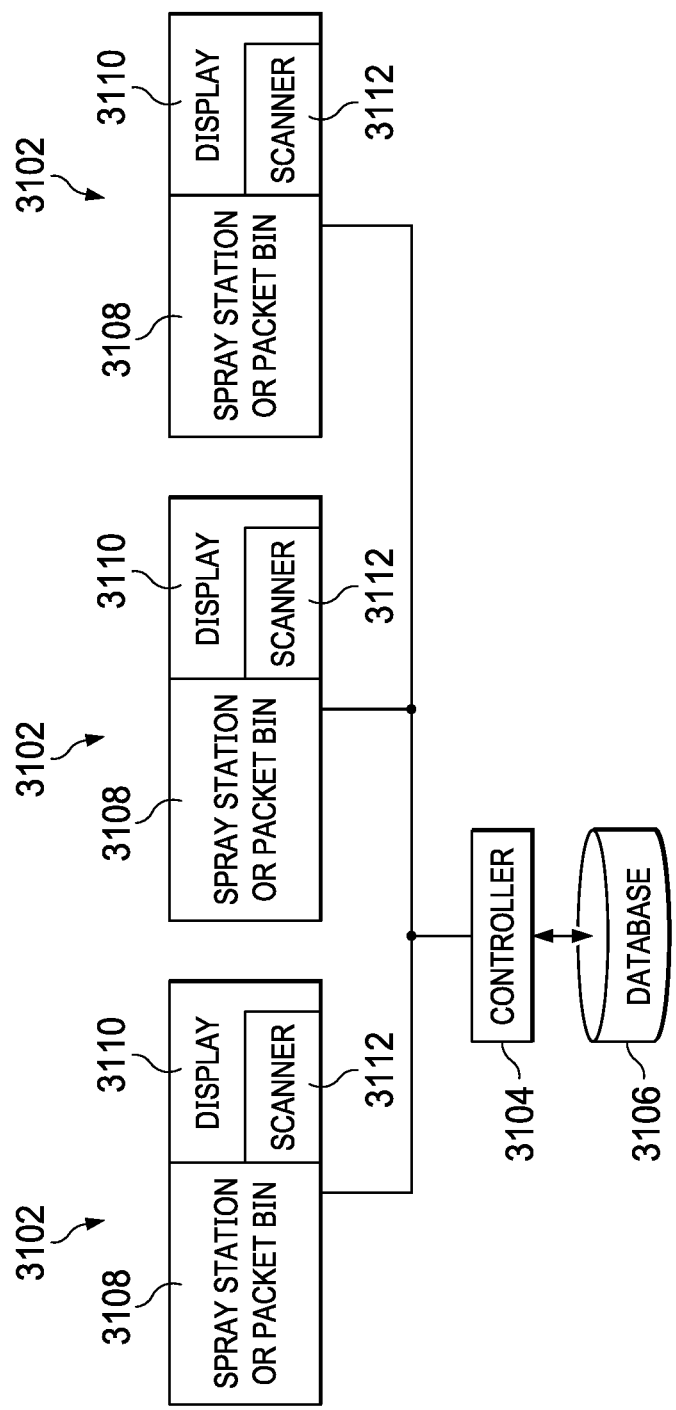
FIG. 31 illustrates a series of testing stations within a line or social distancing path for testing for chemosensory disorders.

The individual chemosensory disorder testing stations may also be strung together in a sequential manner such as a line in order to provide a staged testing of individuals within the line as illustrated in FIG. 31. Each of the testing stations be they manual or digital can be staged along waiting lines or social distancing paths with each station providing a different code to be recognized for results storage purposes. The testing stations are coded in the same manner as individual packets are coded. If the individual packets are provided, the packets could just be grab bag or luck of the draw as long as the individual test two or more scents correctly. The staged testing system would include a plurality of testing stations 3102 that are located along a line or social distancing path. Each of the testing stations 3102 communicate with a central controller 3104 that controls the operations of each of the testing stations as described above. The central controller 3104 is connected with a relational database 3106 that stores the test results received from the testing stations 3102. These test results would be associated with a particular individual identifier such that an individual may generate test results at each of the testing stations 3102 and have the separate results associated together for a final determination of the individual status by the controller 3104.

Each of the testing stations 3102 includes a spray station or packet bin 3108 for dispensing the tests under the control of the central controller 3104. The spray station or packet bin 3108 may be configured in a manner similar to that discussed above with respect to the provision of the test for allowing entry to a venue. Alternatively, the central controller 3104 may cause the testing station 3102 to dispense a particular known packet having a known fragrance associated with the packet. Since the fragrance of the dispensed packet is known the test result may be determined by the controller 3104 responsive to the test response given through a display 3110. Alternatively, rather than dispensing a packet having a known fragrance, a user could merely randomly select a packet from an associated packet bin and then scan a code on the face of the packet wherein the code identifies the fragrance associated with the packet to the central controller 3104 in a manner similar to that described above using an associated scanner 3112.

The scanner 3112 is used for scanning a bar or QR code associated with a ticket or document possessed by an individual or could comprise magnetic or chip card readers for reading a magnetic strip or chip embedded upon a drivers license or other type of ID associated with the individual. Additionally, the scanner 3112 scans codes located on the face of a packet that is selected from the system in order to notify the controller 3104 of the scent associated with the packet without providing this information to the individual being tested. The display 3110 displays various options for the user to select the scent they detected within the scent provided to them. The central controller 3104 controls the display 3110 to display, for example, four different selections wherein only one of the selections accurately identifies the provided scent. The relational database 3106 will store each of the test results received from the individual testing stations 3102. Each test result will be associated with a particular test identifying the smell associated with the test and a unique identifier associated with the individual taking the test.

While FIG. 31 has described that each of the testing stations 3102 are located along a line or social distancing path, the testing stations could also be separated in time from each other. Thus, in order to maintain the validity of an access pass of an individual to, for example, access buildings on a college campus, the test subject would periodically have to go to a testing station and test their sense of smell with one or more tests as described above. After completion of a successful test, the access pass would be validity for an additional period of time (hours, days, etc.).

Figure 32:
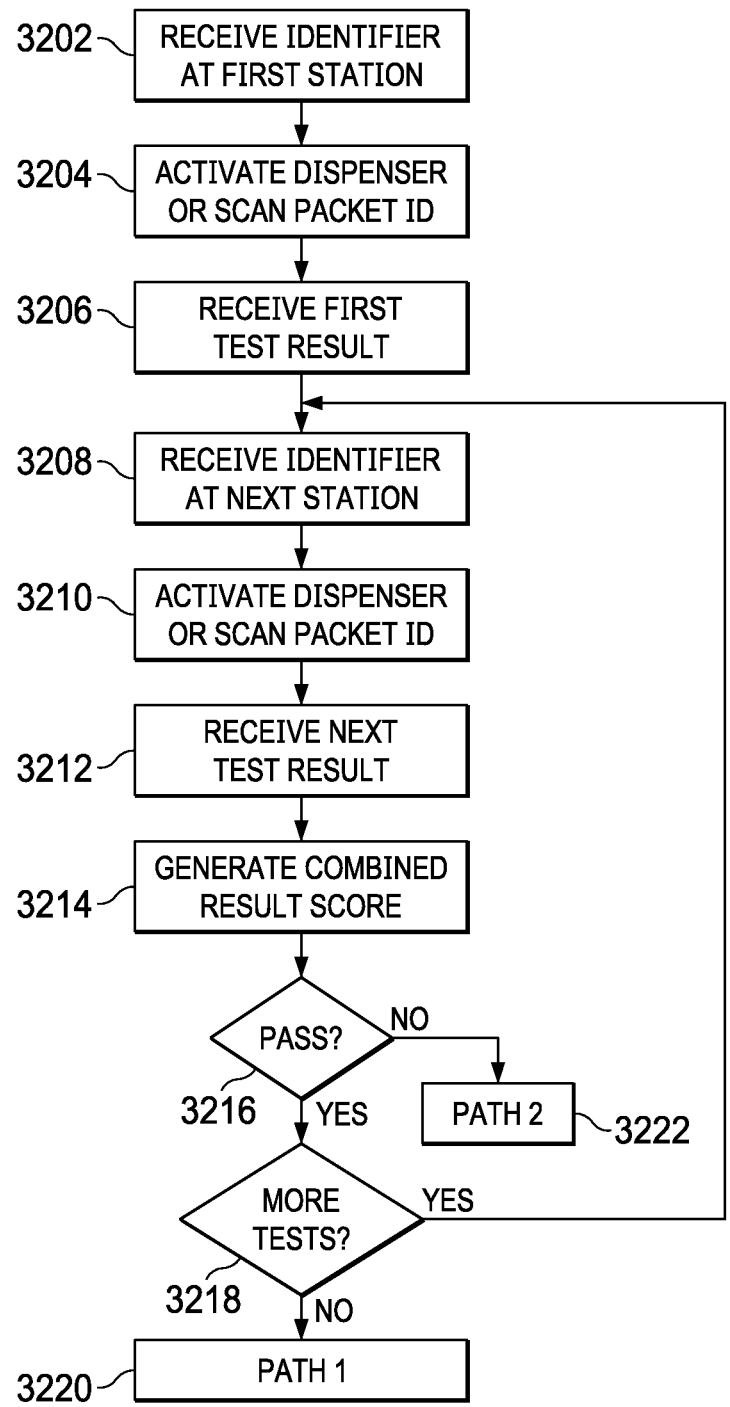
FIG. 32 illustrates a flow diagram of a process for performing staged testing of individuals in a line or social distancing path.

Referring now to FIG. 32 there is illustrated a flow diagram of the process for performing staged testing of individuals in a line or social distancing path. When an individual arrives at a first testing station 3102, the testing station receives the user identifier at step 3202 using for example a scanner 3112 as described previously. Upon receipt of an identifier associated with the test subject, the system will either actuate a spray dispenser using for example a similar system to that described hereinabove with respect to FIG. 19 and others or alternatively, scan a packet ID associated with a testing packet at step 3204. The system will receive the first test result at step 3206 involving the user providing an entry responsive to the scent provided to them through a display 3110 responsive to the scent provided to them and transmission and storage of the user selection of the test result within the relational database 3106 through the controller 3104. The individual next proceeds to a next testing station 3102 and again enters their identifier at the next testing station at step 3208. Responsive to receipt of an identifier, the system activates at step 3210 a dispenser to dispense a scent medium or alternatively scan a packet ID associated with a packet selected by the test subject. The results are entered into the system and received at step 3212 where the user selects a smelled scent using an associated display 3110 providing multiple result selections, and the test result is stored in relational database 3106 associated with the central controller 104. When multiple test results have been received, a combined result score generated at step 3214. The combined result score is based upon multiple tests performed on the individual passing through the line. Inquiry step 3216 determines whether or not the user has passed the multiple tests taken by the individual test subject. If so, control passes to inquiry step 3218 and a determination is made if more testing is needed or available for the individual. If no further testing is available, the individual is sent through path one processing at step 3220 wherein the user would likely be admitted to the location or receive an indication as passing the test since the combined score indicated a passing condition. If more tests are available as determined at inquiry step 3218, control passes back to step 3208 to receive an identifier at the next testing station. If inquiry step 3216 determines from the combined score that the individual has not passed, the test control passes to the path two processing 3222 wherein the user may be denied entry to a facility or required to take further screening processes possibly with medical staff in order to be allowed into the facility or determine whether the failure of the smell test is indicating a particular problem. The path two processing 3222 could also involve the issuance of an approval certificate that would allow an individual access to one or more facilities/locations. The approval certificate could comprise some time of physical certificate dispensed by the system, an indication coded onto a ID associated with the individual or updating a database entry associated with the individual to indicate that they are allowed access.

Figure 33:
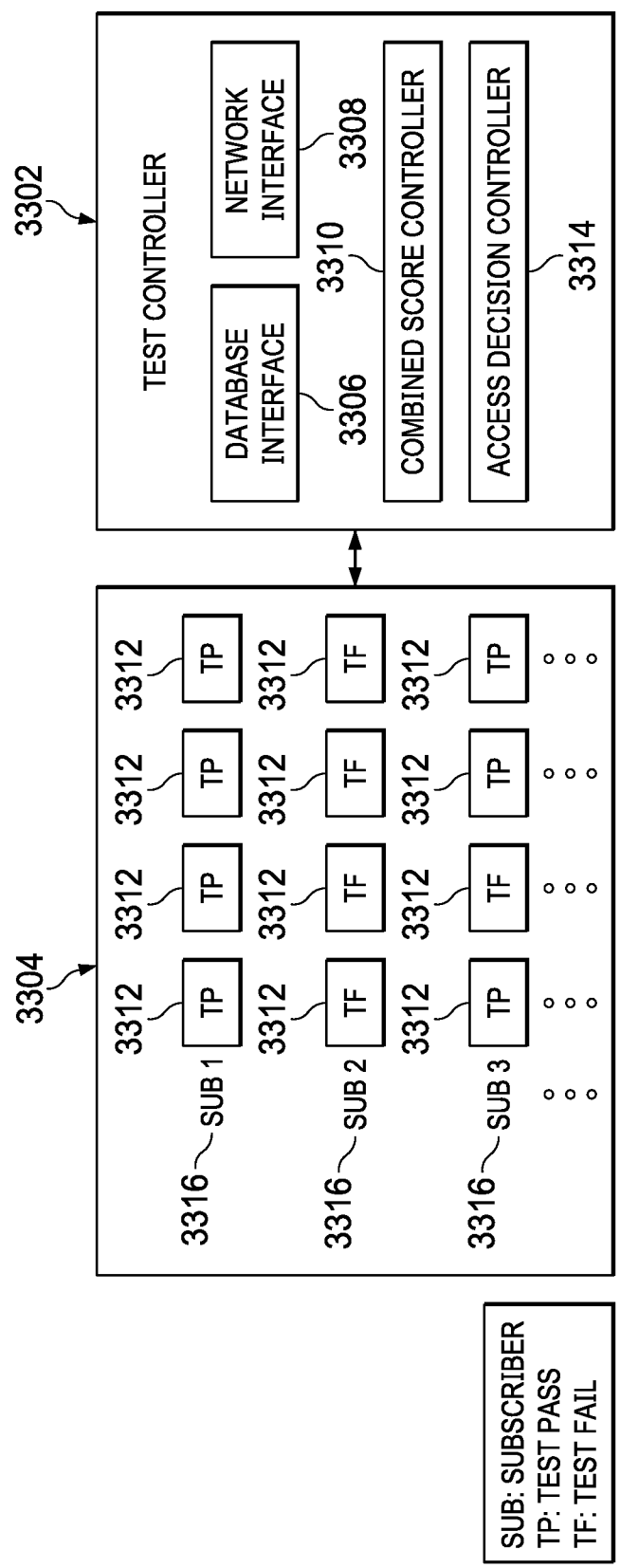
FIG. 33 illustrates a test controller and relational database for providing staged test results for individuals.

Referring now to FIG. 33, there is illustrated a more detailed illustration of the test controller 3302 and relational database 3304 for providing staged test results for an individual. The test controller 3302 comprises a server/processor receiving the test results from multiple locations such as the controller 3104 illustrated in FIG. 31 or could comprise a mobile application implemented on a mobile device, tablet pad, etc. The test controller 3302 includes a database interface 3306 enabling the test controller 3302 to communicate with the relational database 3304. A network interface 3308 enables the test controller 3302 to communicate either with a wired or wireless network. This allows the test controller 3302 to receive communications such as test results from one of the testing stations 3102 or transmitting instructions to dispensers 3108 to control the dispensation of a particular scent/fragrance for testing an individual scent. The combined score controller 3310 takes multiple individual test results provided either through the network interface 3308 from various testing sites or through the network interface and from previously stored test results 3312 stored within the relational database 3304. The combined score controller 3310 computes a combined score based upon each of the tests indicating whether the user has passed or failed or whether or not the tested individual needs to go for further screening or medical attention or if they may be admitted to a particular venue. The decision on how to treat an individual based upon their combined score from the combined score controller 3310 is made by the access decision controller 3314. The access decision controller 3314 will be programmed according to a set of predetermined parameters that establishes what indicates a passed test and what indicates a failed test. For example, if four tests were taken, a pass indication could be established based upon three or more positive test results. However, if only a single or no passing test results were received, the testing individual would fail. An indication of two passed and two fail test result could provide an indication of need for further testing to reach a final decision. Any particular predetermined testing criteria may be established based upon the needs or desires of the particular testing facility or testing station. The basis on which an individual is determined to pass or fail can be dynamically adjusted by the access decision controller such that based on changing conditions or changing factors based on previous test results of the individual the pass/fail criteria can be dynamically changed.

The relational database 3304 stores multiple test results 3312 with respect to various tested individuals. These test results can indicate a test pass (TP) result or a test fail (TF) test result. These results would vary according to the particular individual being tested. Each of the test results 3312 have two specific identifiers associated therewith. The first is the unique ID 3316 associated with each individual being tested. In the example in FIG. 33 there are indicated Sub 1, Sub 2 and Sub 3. Each of these would have a unique identifier associated where there with such that each test within the row of subscriber 1 is associated with subscriber 1. Each test in the row of subscriber 2 is associated with subscriber 2 and so forth. In addition to being associated with the individual identifier, each test 3312 also has associated there with a testing identifier unique to the specific test. This identifier would indicate the original fragrance associated with the test either dispensed by the system using an automatic dispensing system or selected by the user if a selected packet system were used. The test identifier would also identify with the test result indicating whether the individual had passed or failed the test. Thus, each test result would have at least two identifiers associated there with for monitoring and determining test results.

It will be appreciated by those skilled in the art having the benefit of this disclosure that this chemosensory disorder trigger and management system provides a method and system for performing chemosensory disorder testing provides an improved method and apparatus for anosmia prognostic screening. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A system for controlling access to a controlled access location, comprising:
   a scanner for scanning a unique identifier for access to the controlled access location;
   an input display for receiving a response input from an individual based upon scents detected by the individual;
   an automated testing dispenser for dispensing at least one testing scent on each hand of the individual desiring access to the controlled access location responsive to a dispensing control signal;
   a processor coupled to the automated testing dispenser, the scanner and the input display for controlling access to the controlled access location responsive to a stored set of instructions;
   a memory coupled to the processor, the memory having data and the stored set of instructions, the stored set of instructions configuring the processor to:
   receive the unique identifier from the scanner;
   generate the dispensing control signal to actuate the automated testing dispenser to dispense the at least one testing scent responsive to receipt of the unique identifier;
   receive the response input from the individual based on the scents detected by the individual of the at least one testing scent dispensed on their hands;
   determine a passing test result or a failing test result responsive to the received response input and an expected response based on the dispensed at least one testing scent;
   enable access to the controlled access location responsive to a determined passing test result; and
   deny access to the controlled access location responsive to a determined failing test result.

2. The system of claim 1, wherein the automated testing dispenser further comprises:
   a plurality of reservoirs each containing a separate scent of a plurality of scents;
   a pumping mechanism for dispensing a predetermined scent from a selected one of the plurality of reservoirs, the pumping mechanism responsive to the dispensing control signal for dispensing the predetermined scent from one of the plurality of reservoirs; and
   at least two nozzles for dispensing the predetermined scent from the pumping mechanism.

3. The system of claim 1, further comprising:
   a first nozzle and a second nozzle for dispensing a predetermined scent;
   at least one actuator for dispensing from the first nozzle and the second nozzle;
   wherein the stored set of instructions further configure the processor to:
   select the at least one testing scent for dispensing from the first nozzle;
   select a control material for dispensing from the second nozzle; and
   initiate the at least one actuator to dispense the at least one testing scent from the first nozzle and the control material from the second nozzle.

4. The system of claim 3, wherein the stored set of instructions further configure the processor to:
   initiate the at least one actuator to dispense the control material through the first nozzle after the at least one testing scent has been dispensed through the first nozzle to remove the at least one testing scent from the first nozzle.

5. The system of claim 3, wherein the stored set of instructions further configure the processor to select the at least one testing scent from a plurality of scents in a random fashion to change the at least one testing scent selected before each dispensing of the at least one testing scent from the first nozzle.

6. The system of claim 1, wherein the stored set of instructions further configure the processor to:
   provide a plurality of options for selection by the individual on the input display, the plurality of options including one option associated with the at least one testing scent.

7. The system of claim 1, wherein the stored set of instructions further configure the processor to open a gate to enable access to the controlled access location.

8. The system of claim 1, wherein the at least one testing scent is contained within a material selected from a group consisting essentially of a hand sanitizer, a spray and a gel.

9. A method for controlling access to a controlled access location, comprising:
   receiving a unique identifier for access to the controlled access location using a scanner;
   generate a dispensing control signal to actuate an automated testing dispenser to dispense at least one testing scent responsive to receipt of the unique identifier;
   dispensing the at least one testing scent on each hand of an individual desiring access to the controlled access location responsive to the dispensing control signal from the automated testing dispenser;
   receiving a response input from the individual based upon the scents detected by the individual and indicated on an input display;
   determine a passing test result or a failing test result responsive to the received response input and an expected response based on the dispensed at least one scent;
   enabling access to the controlled access location responsive to a determined passing test result; and
   denying access to the controlled access location responsive to a determined failing test result.

10. The method of claim 9, wherein the step of dispensing further comprises:
    storing a separate scent of a plurality of scents in each of a plurality of reservoirs; and
    dispensing a predetermined scent from a selected one of the plurality of reservoirs responsive to the dispensing control signal through at least two nozzles using a pumping mechanism.

11. The method of claim 9, further comprising:
    selecting the at least one testing scent for dispensing from a first nozzle;
    selecting a control material for dispensing from a second nozzle; and initiating at least one actuator to dispense the at least one testing scent from the first nozzle and the control material from the second nozzle.

12. The method of claim 11 further comprising initiating the at least one actuator to dispense the control material through the first nozzle after the at least one testing scent has been dispensed through the first nozzle to remove the at least one testing scent from the first nozzle.

13. The method of claim 11, wherein the step of selecting the at one scent further comprises selecting the at least one testing scent from a plurality of scents in a random fashion to change the at least one testing scent selected before each dispensing of the at least one testing scent from the first nozzle.

14. The method of claim 9 further comprising displaying a plurality of options for selection by the individual on the input display, the plurality of options including one option associated with the at least one testing scent.

15. The method of claim 9, wherein the step of enabling access further comprises the step of opening a gate to enable access to the controlled access location.

16. The method of claim 9, wherein the at least one testing scent is contained within a material selected from a group consisting essentially of a hand sanitizer, a spray and a gel.

17. A system for controlling access to a controlled access location, comprising:
  a scanner for scanning a unique identifier for access to the controlled access location;
  an input display for receiving a response input from an individual based upon scents detected by the individual;
  an automated testing dispenser for dispensing at least one testing scent within a hand sanitizer on each hand of the individual desiring access to the controlled access location responsive to a dispensing control signal, wherein the automated testing dispenser further comprises:
    a plurality of reservoirs each containing a separate scent of a plurality of scents;
    a pumping mechanism for dispensing a predetermined scent from a selected one of the plurality of reservoirs, the pumping mechanism responsive to the dispensing control signal for dispensing the predetermined scent from one of the plurality of reservoirs;
    at least one nozzle for dispensing the predetermined scent from the pumping mechanism;
  a processor coupled to the automated testing dispenser, the scanner and the input display for controlling access to the controlled access location responsive to a stored set of instructions;
  a memory coupled to the processor, the memory having data and the stored set of instructions, the stored set of instructions configuring the processor to:
    receive the unique identifier from the scanner;
    generate the dispensing control signal to actuate the automated testing dispenser to dispense the at least one testing scent within the hand sanitizer responsive to receipt of the unique identifier;
    provide a plurality of options for selection by the individual on the input display, the plurality of options including one option associated with the at least one testing scent;
    receive the response input from the individual based on the scents detected by the individual of the at least one testing scent dispensed on their hands;
    determine a passing test result or a failing test result responsive to the received response input and an expected response based on the dispensed at least one testing scent; and
    open a gate to enable access to the controlled access location responsive to a determined passing test result.

18. The system of claim 17, further comprising:
  wherein the at least one nozzle includes a first nozzle and a second nozzle for dispensing the predetermined scent;
  at least one actuator for dispensing from the first nozzle and the second nozzle;
  wherein the stored set of instructions further configure the processor to:
    select the at least one testing scent for dispensing from the first nozzle;
    select a control material for dispensing from the second nozzle; and
    initiate the at least one actuator to dispense the at least one testing scent from the first nozzle and the control material from the second nozzle.

19. The system of claim 18, wherein the stored set of instructions further configure the processor to:
  initiate the at least one actuator to dispense the control material through the first nozzle after the at least one testing scent has been dispensed through the first nozzle to remove the at least one testing scent from the first nozzle.

20. The system of claim 18, wherein the stored set of instructions further configure the processor to select the at least one testing scent from a plurality of scents in a random fashion to change the at least one testing scent selected before each dispensing of the at least one testing scent from the first nozzle.

* * * * *